United States Patent
Heinrich et al.

(10) Patent No.: US 8,859,581 B2
(45) Date of Patent: Oct. 14, 2014

(54) AZAHETEROCYCLIC COMPOUNDS AS KINASE INHIBITORS

(75) Inventors: Timo Heinrich, Gross-Umstadt (DE); Andree Blaukat, Muehltal (DE); Wolfgang Staehle, Ingelheim (DE); Hartmut Greiner, Weiterstadt (DE); Maria Kordowicz, Griesheim (DE)

(73) Assignee: Merck Patent GmbH, Darmstadt (DE)

( * ) Notice: Subject to any disclaimer, the term of this patent is extended or adjusted under 35 U.S.C. 154(b) by 1708 days.

(21) Appl. No.: 11/912,462

(22) PCT Filed: Mar. 30, 2006

(86) PCT No.: PCT/EP2006/002871
§ 371 (c)(1),
(2), (4) Date: Oct. 24, 2007

(87) PCT Pub. No.: WO2006/114180
PCT Pub. Date: Nov. 2, 2006

(65) Prior Publication Data
US 2008/0176892 A1      Jul. 24, 2008

(30) Foreign Application Priority Data

Apr. 25, 2005 (DE) .......................... 10 2005 019 094
Jan. 19, 2006 (DE) .......................... 10 2006 002 649

(51) Int. Cl.
*C07D 471/04* (2006.01)
*A61K 31/437* (2006.01)

(52) U.S. Cl.
CPC .................................... *C07D 471/04* (2013.01)
USPC .......................................... 514/300; 546/113

(58) Field of Classification Search
USPC .......................................... 546/113; 514/300
See application file for complete search history.

(56) References Cited

U.S. PATENT DOCUMENTS 7,504,509 B2 * 3/2009 Ibrahim et al. ................. 546/113

FOREIGN PATENT DOCUMENTS

| WO | WO 03/000688     |    | 1/2003  |
|----|------------------|----|---------|
| WO | WO 2004/016609 A |    | 2/2004  |
| WO | 2004087704       | *  | 10/2004 |
| WO | WO 2004/099205 A |    | 11/2004 |
| WO | WO 2005/116028 A |    | 12/2005 |

OTHER PUBLICATIONS

Vippagunta et al., "Crystalline Solid", Advanced Drug Delivery Reviews 48 (2001) 3-26.*
Guillory (In Brittain ed), "Polymorphism, etc.," NY: Marcel Dekker, Inc., 1999, 1-2. 183-226.*
Yu et al., "Physical characterization of, etc.," PSTT, vol. 1(3), 118-127 (1998).*
Dorwald , Side Reactions in Organic Synthesis, 2005, Wiley: VCH Weinheim Preface, pp. 1-15 & Chapter 8, pp. 279-308.*
LeRoith et al., The insulin-like growth factor system and cancer, Cancer Letters, 195, pp. 127-137 (2003).*
Simone, Oncology:Introduction, Cecil Textbook of Medicine, ed Bennett et al. W.B.Saunders Co. 20$^{th}$ ed, vol. 1, 1996, pp. 1004-1010.*
Robinson, Medical Therapy of Inflammatory Bowel Disease for the 21st century, Eur. J. Surg. 164, Suppl. 582, pp. 90-98, (1998).*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Lodish et al., "Endocrine side, etc.," Endocrine-Related Cancer (2010) 17, R233-R244.*
Dietz et al., "HDAC inhibitors, etc.," Pharmacological Research 62 (2010) 11-17.*
Ouaissi et al., "Rationale for Possible, etc.," Journal of Biomedicine and Biotechnology, 2011, Article: ID 315939, 1-8.*
Golub et al, Science, vol. 286, Oct. 15, 1999, pp. 531-537.*

* cited by examiner

Primary Examiner — Patricia L Morris
(74) Attorney, Agent, or Firm — Millen, White, Zelano & Branigan, P.C.

(57) ABSTRACT

The invention relates to compounds of the formula (I), to the preparation and use thereof for the preparation of a medicament for the treatment of diseases, in particular tumors and/or diseases in the development or course of which kinases are involved.

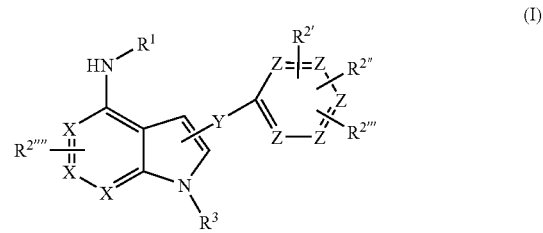

21 Claims, No Drawings

AZAHETEROCYCLIC COMPOUNDS AS KINASE INHIBITORS

The invention relates to compounds of the formula I

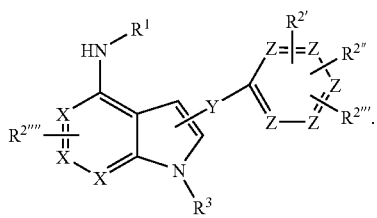

in which
- $R^1$ denotes H, A, Ar, Ar-A or A-Ar,
- A denotes unbranched, branched or cyclic alkyl having 1-14 C atoms, in which one or two $CH_2$ groups may be replaced by an O or S atom and/or by an NH, NA, CONH, NHCO or —CH=CH— group and/or, in addition, 1-7 H atoms may be replaced by Hal, and in which one or two $CH_3$ groups may be replaced by $NH_2$, NAH, $NA_2$, NHCOOA, NHCONHA, NHCONHAr or CN,
- Ar denotes a mono- or bicyclic aromatic homo- or heterocycle having 1 to 4 N, O and/or S atoms and 5 to 10 skeleton atoms, which may be unsubstituted or mono-, di- or trisubstituted by carbonyl oxygen, Hal, A, OH, OA, $NH_2$, NHA, $NA_2$, $NO_2$, CN, OCN, SCN, COOH, COOA, $CONH_2$, CONHA, $CONA_2$, NHCOA, $NHCONH_2$, $NHSO_2A$, CHO, COA, $SO_2NH_2$ and/or $S(O)_gA$,
- Ar-A denotes aryl-alkyl
- A-Ar denotes alkyl-aryl
- Hal denotes F, Cl, Br or I,
- X denotes CH or N, where one group X in each compound of the formula I is N and two groups X are CH,
- Y denotes $CH_2$ or a saturated bond,
- Z denotes CH or N, where at most two groups Z in each compound of the formula I are N and preferably one or no group Z is N,
- $R^{2'}$, $R^{2''}$, $R^{2'''}$, $R^{2''''}$ each, independently of one another, denote H, Hal, OH, CN, $NH_2$, unbranched or branched alkyl having 1-4, 5 or 6 C atoms, in which one $CH_2$ group may be replaced by an O or S atom and/or by an NH, NA, CONH, NHCO or —CH=CH— group and/or, in addition, 1-4 H atoms may be replaced by Hal, and in which one $CH_3$ group may be replaced by $NH_2$, NAH, $NA_2$, CN or Ar,
- $R^3$ denotes H, A or Ar-A,
- g denotes 0, 1 or 2 and
- ---- denotes a single or double bond, and pharmaceutically acceptable salts, derivatives, solvates and stereoisomers thereof, including mixtures thereof in all ratios.

It has been found that the compounds of the formula I are capable of inhibiting, regulating and/or modulating signal transduction mediated by kinases, in particular by tyrosine kinases. In particular, the compounds according to the invention are suitable as inhibitors of tyrosine kinases. Thus, medicaments and pharmaceutical compositions according to the invention can be effectively employed for the treatment of diseases that are caused, mediated and/or propagated by kinases and/or by kinase-mediated signal transduction. Thus, the compounds according to the invention are suitable for the treatment and prophylaxis of cancer, tumour growth, arteriosclerosis, diabetic retinopathy, inflammatory diseases, psoriasis and the like in mammals.

BACKGROUND OF THE INVENTION

Cancer is a disease whose causes are to be seen, inter alia, in disturbed signal transduction. In particular, deregulated signal transduction via tyrosine kinases plays a central role in the growth and spread of cancer (Blume-Jensen, P. and T. Hunter, Nature 411: 355-365, 2001; Hanahan D. and R. A. Weinberg, Cell 100:57-70, 2000). Tyrosine kinases and in particular receptor tyrosine kinases and the growth factors binding to them may thus be involved in deregulated apoptosis, tissue invasion, metastasis and generally in signal transduction mechanisms which lead to cancer.

As already mentioned, one of the principal mechanisms by which cellular regulation is effected is the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is a very widespread process within cells and since cellular phenotypes are largely influenced by the activity of these pathways, it is currently believed that a large number of conditions and/or diseases are attributable to either aberrant activation or functional mutations in the molecular components of kinase cascades. Consequently, considerable attention has been devoted to the characterisation of these proteins and compounds that are able to modulate their activity (see review article: Weinstein-Oppenheimer et al., Pharma. &. Therap. 88:229-279, 2000). Various possibilities for the inhibition, regulation and modulation of kinases encompass, for example, the provision of antibodies, antisense ribozymes and inhibitors. In oncology research, tyrosine kinases, in particular, are highly promising targets. Thus, numerous synthetic small molecules are undergoing clinical development as tyrosine kinase inhibitors for the treatment of cancer, for example Iressa® or Gleevec®. However, numerous problems, such as side effects, dosage, resistance of the tumour, tumour specificity and patient selection, still have to be solved here.

Tyrosine kinases are a class of enzymes which catalyse the transfer of the terminal phosphate of adenosine triphosphate to tyrosine residues in protein substrates. It is thought that tyrosine kinases, through substrate phosphorylation, play a crucial role in signal transduction for a number of cellular functions. Although the precise mechanisms of signal transduction are still unclear, tyrosine kinases have been shown to be important factors in cell proliferation, carcinogenesis and cell differentiation.

Tyrosine kinases can be categorized as receptor tyrosine kinases or non-receptor tyrosine kinases. Receptor tyrosine kinases have an extracellular portion, a transmembrane portion and an intracellular portion, while non-receptor tyrosine kinases are exclusively intracellular.

Receptor tyrosine kinases consist of a multiplicity of transmembrane receptors with different biological activity. Thus, about 20 different subfamilies of receptor tyrosine kinases have been identified. One tyrosine kinase subfamily, known as the EGFR or HER subfamily, consists of EGFR, HER2, HER3 and HER4. Ligands from this subfamily of receptors include epithelial growth factor (EGF), tissue growth factor (TSF-α), amphi-regulin, HB-EGF, betacellulin and heregulin. Another subfamily of these receptor tyrosine kinases is the insulin subfamily, which includes INS-R, IGF-IR and IR-R. The PDGF subfamily includes the PDGF-α and -β receptor, CSFIR, c-kit and FLK-II. In addition, there is the FLK family, which consists of the kinase insert domain receptor (KDR) or VEGFR-2, foetal liver kinase-1 (FLK-1), foetal liver kinase-4 (FLK-4) and fms tyrosine kinase-1 (fit-1) or VEGFR-1. The PDGF and FLK family are usually combined in the group of the split kinase domain receptor tyrosine kinases (Laird, A. D. and J. M. Cherrington, Expert. Opin. Investig. Drugs 12(1):51-64, 2003) due to the similarities between the two groups. For a detailed discussion of receptor tyrosine kinases, see the paper by Plowman et al., DN & P 7(6):334-339, 1994).

Non-receptor tyrosine kinases likewise consist of a multiplicity of subfamilies, including Src, Frk, Btk, Csk, Abl, Zap70, Fes/Fps, Fak, Jak, Ack, and LIMK. Each of these subfamilies is further sub-divided into different sub-groups. For example, the Src subfamily is one of the largest subfamilies. It includes Src, Yes, Fyn, Lyn, Lck, Blk, Hck, Fgr and Yrk. The Src subfamily of enzymes has been linked to oncogenesis. For a more detailed discussion of non-receptor tyrosine kinases, see the paper by Bolen, Oncogene, 8:2025-2031, 1993.

Both receptor tyrosine kinases and non-receptor tyrosine kinases are involved in cellular signal transfer pathways leading to conditions such as cancer, psoriasis and hyperimmune responses.

The present invention relates to compounds of the formula I, preferably as regulators, modulators or inhibitors of receptor tyrosine kinases of the insulin subfamily, which includes the insulin receptor IR, the "insulin like growth factor-1 receptor" IGF-1R and the "insulin related receptor" IRR. The compounds according to the invention are particularly effective in the inhibition of the receptor tyrosine kinase IGF-1R.

As previously mentioned, the insulin-like growth factor-1 receptor (IGF-1R) belongs to the family of transmembrane tyrosine kinase receptors, such as platelet-derived growth factor receptor, the epidermal growth factor receptor, and the insulin receptor. There are two known ligands for the IGF-1R receptor. They are IGF-1 and IGF-2. As used herein, the term "IGF" refers to both IGF-1 and IGF-2. A review of the insulin-like growth factor family of ligands, receptors and binding proteins is given in Krywicki and Yee, Breast Cancer Research and Treatment, 22:7-19, 1992.

IGF/IGF-1R-induced diseases are characterised by an anomalous activity or hyperactivity of IGF/IGF-1R. Anomalous IGF activity refers to either: (1) IGF or IGF-1R expression in cells which do not normally express IGF or IGF-1R; (2) increased IGF or IGF-1R expression leading to undesired cell proliferation, such as cancer; (3) increased IGF or IGF-1R activity leading to undesired cell proliferation, such as cancer, and/or hyperactivity of IGF or IGF-1R. Hyperactivity of IGF or IGF-1R refers to either an amplification of the gene encoding IGF-1, IGF-2, IGF1R or the production of a level of ISF activity which can be correlated with a cell proliferative disease (i.e. as the level of IGF increases, the severity of one or more symptoms of the cell proliferative disease increases) the bioavailability of ISF-1 and IGF-2 can also be affected by the presence or absence of a set of IGF binding proteins (IGF-BPs) of which six are known. Hyperactivity of IGF/IGF-1R can also result from downregulation of IGF-2 which contains an IGF-2 binding domain, but no intracellular kinase domain. Examples of IGF/IGF-1R-induced diseases include the various IGF/IGF-1R-related human malignancies reviewed in Cullen et al., Cancer Investigation, 9(4):443-454, 1991. For the clinical importance and role of IGF/IGF-IRs in regulating osteoblast function, see Schmid, Journal of Internal Medicine, 234:535-542, 1993.

The activities of IGF-1R thus include: (1) phosphorylation of IGF-1R protein; (2) phosphorylation of an ISF-1R protein substrate; (3) interaction with an IGF adapter protein; (4) IGF-1R protein surface expression. Further IGF-1R protein activities can be identified using standard techniques. IGF-1R activity can be assayed by measuring one or more of the following activities: (1) phosphorylation of IGF-1R; (2) phosphorylation of an IGF-1R substrate; (3) activation of an IGF-1R adapter molecule and (4) activation of downstream signalling molecules and/or (5) increased cell division.

These activities can be measured using techniques described below and known in the prior art.

IGF-1R has been regarded as essential for the establishment and maintenance of the transformed phenotype in vitro and in vivo in a number of cell types (R. Baserga, Cancer Research 55:249-252, 1995). Herbimycin A has been said to inhibit ISF-1R protein tyrosine kinase and cell proliferation in human breast cancer cells (Sepp-Lorenzino et al., J. Cell Biochem. Suppl. 18b:246, 1994). Experiments studying the role of IGF-1R in transformation that have used antisense strategies, dominant negative mutations, and antibodies to IGF-1R have led to the hypothesis that IGF-1R may be a preferred target for therapeutic interventions.

In addition to its role in nutritional support and in type-II diabetes, IGF-1R has also been associated with several types of cancer. For example, IGF-1 has been implicated as an autocrine growth stimulator for several tumour types, e.g. human breast cancer carcinoma cells (Arteago et al., J. Clin. Invest., 84:1418-1423, 1989) and small lung tumour cells (Macauley et al., Cancer Res., 50:2511-2517, 1989). In addition, IGF-1, while integrally involved in the normal growth and differentiation of the nervous system, also appears to be an autocrine stimulator of human gliomas. Sandberg-Nordqvist et al., Cancer Res., 53:2475-2478, 1993.

An example of the potential involvement of IGF-2 in colorectal cancer may be found in the upregulation of IGF-2 mRNA in colon tumours relative to normal colon tissues (Zhang et al., Science:276: 1268-1272, 1997) IGF-2 may also play a role in hypoxia-induced neovascularisation of tumours. (Mines et al., Int. J. Mol. Med. 5:253-259, 2000) IGF-2 may also play a role in tumourigenesis through activation of an insulin receptor isoform A. IGF-2 activation of insulin receptor isoform A activates cell survival signalling pathways, but its relative contribution to tumour cell growth and survival is unknown at this time. The kinase domain of insulin receptor isoform A is identical to that of the standard insulin receptor (Scalia et al., J. Cell Biochem. 82:610-618, 2001).

The importance of IGF-1R and its ligands in cell types in culture (fibroblasts, epithelial cells, smooth muscle cells, T-lymphocytes, myeloid cells, chondrocytes and osteoblasts (the stem cells of the bone marrow)) is illustrated by the ability of IGF-1 to stimulate cell growth and proliferation (Goldring and Goldring, Eukaryotic Gene Expression, 1:301-326, 1991). In a series of recent publications, Baserga et al. suggest that IGF-1R plays a central role in the mechanism of transformation and, as such, could be a preferred target for therapeutic interventions in a broad range of human malignant diseases (Baserga, Cancer Res., 55:249-252, 1995; Baserga, Cell, 79:927-930, 1994; Coppola et al., Mol. Cell.

Biol., 14:4588-4595, 1994; Baserga, Trends in Biotechnology, 14:150-152, 1996; H. M. Khandwala et al., Endocrine Reviews, 21:215-244, 2000).

The most important types of cancer that can be treated using a compound according to the invention include breast cancer, prostate cancer, colorectal cancer, small-cell lung cancer, non-small-cell lung cancer, multiple myeloma and renal cell carcinoma and endometrial carcinoma.

IGF-1 has also been associated with retinal neovascularisation. Proliferative diabetic retinopathy has been observed in some patients having high levels of IGF-1. (L. E. Smith et al., Nature Medicine, 5:1390-1395, 1999)

However, the compounds according to the invention may also be suitable as anti-ageing agents. It has been observed that there is a link between IGF signalling and ageing. Experiments have shown that calorie-restricted mammals have low levels of insulin and IGF-1 and have a longer life span. Similar observations have also been made in the case of insects (see C. Kenyon, Cell, 105:165-168, 2001; F. Strauss, Science, 292:41-43, 2001; K. D. Kimura et al., Science, 277:942-946, 1997; M. Tatar et al., Science, 292:107-110, 2001).

The present invention thus also relates to the use of the compounds of the formula I for the prevention and/or treatment of diseases in connection with unregulated or disturbed receptor activity. In particular, the compounds according to the invention can therefore be employed in the treatment of certain forms of cancer, such as, for example, breast cancer, prostate cancer, intestinal cancer, small-cell and non-small-cell lung cancer, multiple myeloma, renal-cell carcinoma or corpus carcinoma.

Also conceivable is the use of the compounds according to the invention for the treatment of diabetic retinopathy or for delaying the ageing process, In particular, they are suitable for use in diagnostic methods for diseases in connection with unregulated or disturbed IGF-1R activity.

In addition, the compounds according to the invention can be used to achieve additive or synergistic effects in certain existing cancer chemotherapies and radiotherapies and/or for restoring the efficacy of certain existing cancer chemotherapies and radiotherapies.

A number of azaindole compounds have hitherto been described as kinase inhibitors, for example in WO 02/092603, WO 04/043388 or WO 04/016609.

The invention was now based on the object of finding novel compounds having advantageous therapeutic properties which can be used for the preparation of medicaments.

Thus, the identification and provision of chemical compounds which specifically inhibit, regulate and/or modulate tyrosine kinase signal transduction is desirable and therefore an aim of the present invention.

DESCRIPTION OF THE INVENTION

It has been found that the compounds of the formula I and salts thereof have very valuable pharmacological properties while being well tolerated. In particular, it has been found that the compounds of the formula I according to the invention surprisingly are effective kinase inhibitors, exhibiting, in particular, a tyrosine kinase-inhibiting action and particularly an IGF-R1-inhibiting action.

In general, all radicals which occur more than once may be identical or different, i.e. are independent of one another. Above and below, the radicals and parameters have the meanings indicated for the formula I, unless expressly indicated otherwise.

Accordingly, the invention relates, in particular, to the compounds of the formula I in which at least one of the said radicals has one of the preferred meanings indicated below.

Hal denotes fluorine, chlorine, bromine or iodine, in particular fluorine or chlorine.

A denotes alkyl, is unbranched (linear), branched or cyclic, and has 1, 2, 3, 4, 5, 6, 7, 8, 9, 10, 11, 12, 13 or 14 C atoms.

Thus, A denotes, for example, methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, linear or branched heptyl, octyl, nonyl or decyl.

A preferably denotes alkyl having 1, 2, 3, 4, 5 or 6 C atoms, in which one or two $CH_2$ groups may be replaced by O or S atoms and/or by NH, NA, CONH, NHCO or —CH=OH- groups and/or in addition 1-7 H atoms may be replaced by F and/or Cl, such as, for example, methyl, ethyl, propyl, isopropyl, butyl, isobutyl, sec-butyl, tert-butyl, pentyl, hexyl, trifluoromethyl, pentafluoroethyl, 1,1-difluoromethyl, 1,1,1-trifluoroethyl, methoxy, ethoxy, n-propoxy, isopropoxy, n-butoxy, isobutoxy, sec-butoxy or tert-butoxy, and in which one or two CH3 groups may be replaced by $NH_2$, NAH, $NA_2$ or CN, such as, for example, N,N'-dimethylaminoalkyl, 2-aminoethyl, 3-aminopropyl, 4-aminobutyl, 5-aminopentyl, 3-aminomethylcyclobutyl, cyanoalkyl, (isoindole-1,3-dion)2-yl or (tert-butyl carbamate)butyl.

Cycloalkyl preferably denotes cyclopropyl, cyclobutyl, cyclopentyl, cyclohexyl or cycloheptyl.

Ar, Ar-A (aryl-alkyl) and A-Ar (alkyl-aryl) denote, for example, unsubstituted phenyl, naphthyl or biphenyl, furthermore preferably, for example, phenyl, naphthyl or biphenyl, each of which is mono-, di- or trisubstituted by A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl.

Ar, Ar-A and A-Ar furthermore denote phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonyl-phenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4- bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl, (4-methoxyphenyl)methyl, (3-methoxyphenyl)methyl, (4-methoxyphenyl)ethyl, (3-methoxyphenyl)ethyl.

Ar, Ar-A and A-Ar furthermore preferably denote 2-, 3- or 4-phenyl, 2-, 3- or 4-phenylmethyl, 2-, 3- or 4-phenylethyl, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 3- or 4-pyridylmethyl, 2-, 3- or 4-pyridylethyl, 2-, 4-, 5- or 6-pyrimidinyl, 2-, 3-, 5-, or 6-pyrazin-1- or 4-yl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, 1-, 2-, 3-, 4-, 5-, 6- or 7-indolyl, 2-, 3-, 4- or 5-isoindolyl, 2-, 6-, or 8-purinyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 3-, 4-, 5-, 6-, 7- or 8-isoquinolinyl, 3-, 4-, 5-, 6-, 7- or 8-quinolinyl, 2-, 4-, 5-, 6-, 7- or 8-quinazolinyl, 5- or 6-quinoxalinyl, 4-, 5-, or 6-phthalazinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl, each of which is unsubstituted or mono-, di- or trisubstituted, for example, by carbonyl oxygen, F, Cl, Br, methyl, ethyl, propyl, phenyl, benzyl, —CH$_2$-cyclohexyl, hydroxyl, methoxy, ethoxy, amino, methylamino, dimethylamino, nitro, cyano, carboxyl, methoxycarbonyl, aminocarbonyl, methylaminocarbonyl, dimethylaminocarbonyl, acetamino, ureido, methylsulfonylamino, formyl, acetyl, amino-sulfonyl and/or methylsulfonyl.

The heterocyclic radicals may also be partially or fully hydrogenated and also denote, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-,-3-,-4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 2-, 3-, 5- or 6-piperidin-1 or 4-yl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-di-hydrobenzofuranyl or 2,3-dihydro-2-oxofuranyl.

The term "substituted" preferably relates to the substitution by the above-mentioned substituents, where a plurality of different degrees of substitution are possible, unless indicated otherwise.

All physiologically acceptable salts, derivatives, solvates and stereoisomers of these compounds, including mixtures thereof in all ratios, are also in accordance with the invention.

The compounds of the formula I may have one or more centres of chirality. They may accordingly occur in various enantiomeric forms and be in racemic or optically active form. The invention therefore also relates to the optically active forms (stereoisomers), the enantiomers, the racemates, the diastereomers and hydrates and solvates of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

An elegant method for the resolution of racemates containing ester groups (for example acetyl esters) is the use of enzymes, in particular esterases.

In the compounds of the formula I, the group

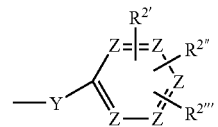

is preferably linked to the group derived from indole or 2,3-dihydroindole via the 2- or 3-position corresponding to the indole nomenclature.

A preferred group of compounds of the formula I conforms to the formula Ia

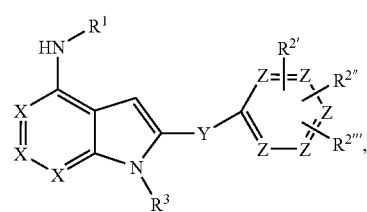

Ia in which $R^1$, $R^2$, $R^3$, Y and Z have the meaning indicated for the formula I, and pharmaceutically acceptable salts, derivatives, solvates and stereoisomers thereof, including mixtures thereof in all ratios.

A further preferred group of compounds of the formula Ia conforms to the formula AII

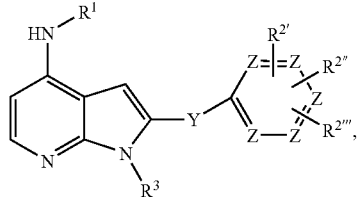

AII in which $R^1$, $R^2$, $R^3$, Y and Z have the meaning indicated for the formula I or Ia, and pharmaceutically acceptable salts, derivatives, solvates and stereoisomers thereof, including mixtures thereof in all ratios.

A further preferred group of compounds of the formula AII conforms to the formula AIII

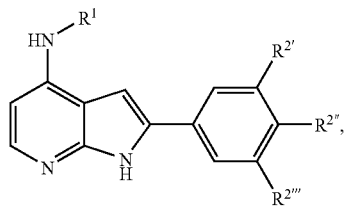

AIII in which Y denotes a bond, Z denotes CH, $R^3$ denotes H, and $R^1$ and $R^2$ have the meaning indicated for the formula I, Ia or AII, and pharmaceutically acceptable salts, derivatives, solvates and stereoisomers thereof, including mixtures thereof in all ratios.

Further preferred sub-groups of compounds of the formula I, Ia, AII and AIII can be expressed by the following sub-formulae Aa to Ag, which correspond to the formulae I, Ia, AII and AIII, but in which in the sub-formula Aa $R^1$ denotes phenyl, phenylcarbonyl, phenylmethyl, pyridyl, pyridylmethyl, pyridylethyl, pyrimidyl, piperazyl, quinoliny, imidazoyl, imidazyolpropyl, pyrrolyl, pyrrolylethyl, each of which is unsubstituted or mono- or polysubstituted by Hal, cyano, methyl, $CHal_3$ or methoxy, furthermore H, N,N'-dimethylaminopropyl or cyanobutyl or one of the following radicals

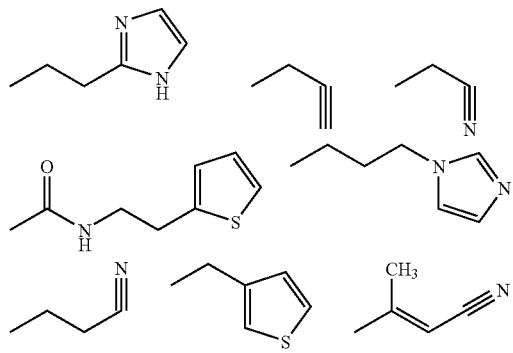

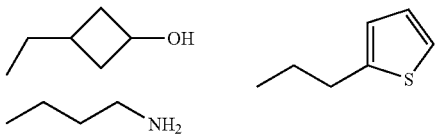

where the linking to the parent structure of the formulae I, Ia, AII or AIII in each case takes place via the bond to the left, which is not a methyl group, and $R^2$, $R^3$ have the meaning indicated for the formula I, in the sub-formula Ab $R^{2'}$, $R^{2''}$, $R^{2'''}$ each, independently of one another, denote H, methoxy, ethoxy, n-propoxy, i-propoxy, 2-phenylethoxy, 3-phenylpropoxy or 4-phenylbutoxy and $R^1$, $R^3$ have the meaning indicated for the formula I, in the sub-formula Ac $R^{2'}$, $R^{2''}$, $R^{2'''}$ each, independently of one another, denote H, methoxy or 3-phenylpropoxy and $R^1$, $R^3$ have the meaning indicated for the formula I, in the sub-formula Ad $R^{2'}$, $R^{2''}$, $R^{2'''}$ each denote methoxy and $R^1$, $R^3$ have the meaning indicated for the formula I, in the sub-formula Ae $R^{2'}$, $R^{2''}$, $R^{2'''}$ each, independently of one another, denote H, methoxy, ethoxy, n-propoxy, i-propoxy, 2-phenylethoxy, 3-phenylpropoxy or 4-phenylbutoxy and $R^1$, $R^3$ have the meaning indicated for the sub-formula Aa, in the sub-formula Af $R^{2'}$, $R^{2''}$, $R^{2'''}$ each, independently of one another, denote H, methoxy or 3-phenylpropoxy and $R^1$, $R^3$ have the meaning indicated for the sub-formula Aa, in the sub-formula Ag $R^{2'}$, $R^{2''}$, $R^{2'''}$ each denote methoxy and $R^1$, $R^3$ have the meaning indicated for the sub-formula Aa and pharmaceutically acceptable salts, derivatives, solvates and stereoisomers thereof, including mixtures thereof in all ratios.

A further preferred group of compounds of the formula I conforms to the formula BII

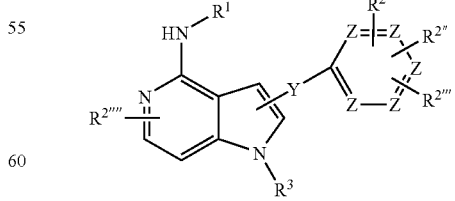

in which $R^1$, $R^2$, $R^3$, Y and Z have the meaning indicated for the formula I, and pharmaceutically acceptable salts, derivatives, solvates and stereoisomers thereof, including mixtures thereof in all ratios.

A further preferred group of compounds of the formula BII conforms to the formula BIII

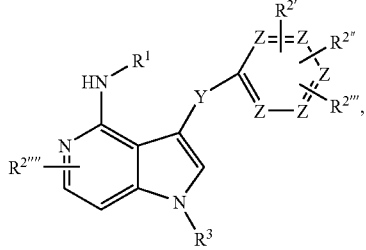

BIII in which all radicals have the meaning indicated for the formula BII.

A still further preferred group of compounds of the formula BIII conforms to the formula BIV

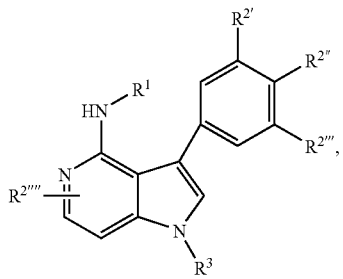

BIV in which Y denotes a bond, Z denotes CH, and $R^1$, $R^2$ and $R^3$ have the meaning indicated for the formula I, BII or BIII, and pharmaceutically acceptable salts, derivatives, solvates and stereoisomers thereof, including mixtures thereof in all ratios.

An even more strongly preferred group of compounds of the formula BIV conforms to the formula BV

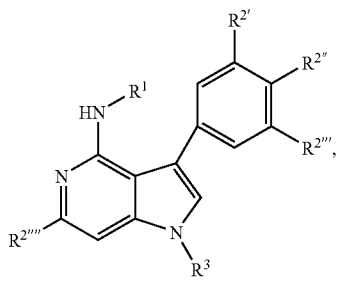

BV in which all radicals have the meaning indicated for the formula BIV, and pharmaceutically acceptable salts, derivatives, solvates and stereoisomers thereof, including mixtures thereof in all ratios.

Further preferred sub-groups of compounds of the formula I, BII, BII BIV and BV can be expressed by the following sub-formulae Ba to Bg, which correspond to the formulae I, BII, BIII, BIV and BV, but in which
in the sub-formula Ba
$R^1$ denotes phenyl, phenylmethyl, pyridyl, pyridylmethyl, pyridylethyl, pyrimidyl, piperazyl, quinoliny, imidazoyl, imidazyolpropyl, pyrrolyl, pyrrolylethyl, each of which is unsubstituted or mono- or polysubstituted by Hal, cyano, methyl or methoxy, and H
and $R^2$ and $R^3$ have the meaning indicated for the formula I,
in the sub-formula Bb
$R^{2'}$, $R^{2''}$, $R^{2'''}$ each, independently of one another, denote H, methoxy, ethoxy, n-propoxy₅ i-propoxy, phenylmethoxy or phenylethoxy,
$R^{2''''}$ denotes H, Hal or $NH_2$
and $R^1$ and $R^3$ have the meaning indicated for the formula I,
in the sub-formula Bc
one of the radicals $R^{2'}$, $R^{2''}$, $R^{2'''}$ denotes methoxy or phenylmethoxy and the other two denote H
and $R^1$ and $R^3$ have the meaning indicated for the formula I,
in the sub-formula Bd
$R^3$ denotes 2-aminoethyl, 3-aminopropyl, 4-aminobutyl, 5-aminopentyl, 3-aminomethylcyclobutyl, (isoindole-1,3-dion)2-yl or 4-(tert-butyl carbamate) but-1-yl
and $R^1$ and $R^2$ have the meaning indicated for the formula I,
in the sub-formula Be
$R^{2'}$, $R^{2''}$, $R^{2'''}$ each, independently of one another, denotes H, methoxy, ethoxy, n-propoxy, i-propoxy, phenylmethoxy or phenylethoxy,
$R^{2''''}$ denotes H, Cl or $NH_2$,
$R^1$ denotes phenyl, phenylmethyl, pyridyl, pyridylmethyl, pyridylethyl, pyrimidyl, piperazyl, quinoliny, imidazoyl, imidazyolpropyl, pyrrolyl, pyrrolylethyl, each of which is unsubstituted or mono- or polysubstituted by Hal, cyano, methyl or methoxy, and H and
$R^3$ denotes 2-aminoethyl, 3-aminopropyl, 4-aminobutyl, 5-aminopentyl, 3-aminomethylcyclobutyl, (isoindole-1,3-dion)2-yl or 4-(tert-butyl carbamate)but-1-yl,
in the sub-formula 3f
one of the radicals $R^{2'}$, $R^{2''}$, $R^{2'''}$ denotes methoxy or phenylmethoxy and
the other two denote H
$R^1$ denotes H, pyridyl, pyridylmethyl or (4-methoxyphenyl)methyl and
$R^3$ denotes 2-aminoethyl, 3-aminopropyl, 4-aminobutyl, 5-aminopentyl, 3-aminomethylcyclobutyl, (isoindole-1,3-dion)2-yl or 4-(tert-butyl carbamate)but-1-yl,
in the sub-formula Bg
one of the radicals $R^{2'}$, $R^{2''}$, $R^{2'''}$ denotes methoxy or phenylmethoxy and the other two denote H
$R^1$ denotes H, pyrid-2 or 3-yl, pyrid-2 or 3-ylmethyl or (4-methoxyphenyl)methyl and
$R^3$ denotes 2-aminoethyl, 3-amino-n-propyl, 4-amino-n-butyl, 5-amino-n-pentyl, 3-aminomethylcyclobut-1-yl, (isoindole-1,3-dion)2-yl or 4-(tert-butyl carbamate)but-1-yl
and pharmaceutically acceptable salts, derivatives, solvates and stereoisomers thereof, including mixtures thereof in all ratios.

Particular preference is given to compounds selected from the compounds listed in Table 1 and pharmaceutically acceptable salts, derivatives, solvates and stereoisomers thereof, including mixtures thereof in all ratios.

The melting points indicated in Table 1 relate, so long as an anion is not indicated, to the free base. In the cases where the melting point cannot be determined owing to decomposition, a decomposition temperature is indicated. If a compound cannot be obtained in crystalline form, the material nature at room temperature is indicated (oil or resin).

TABLE 1

| | | IC50 (μM), IGF1R | Melting point |
|---|---|---|---|
| 1 | (structure) | 14 | 227-228.5° C. (dihydrochloride) |
| 2 | (structure) | 0.76 | 202-203° C. (dihydrochloride hydrate) |
| 3 | (structure) | 0.99 | 78-80° C. (trihydrochloride trihydrate) |
| 4 | (structure) | 0.86 | 80-81° C. |

TABLE 1-continued

| | | IC50 (μM), IGF1R | Melting point |
|---|---|---|---|
| 5 | (structure) | | 267.5-269° C. (hydrochloride) |
| 6 | (structure) | | 164-165° C. (hydrochloride) |
| 7 | (structure) | 0.76 | 292-294° C. (dihydrochloride hydrate) |
| 8 | (structure) | 0.93 | 181.5-183° C. (dihydrochloride dihydrate) |

TABLE 1-continued
| | | IC50 (μM), IGF1R | Melting point |
|---|---|---|---|
| 9 | 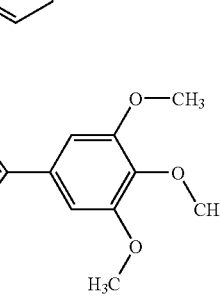 | 1.2 | 105.5-106.5° C. (dihydrochloride dihydrate) |
| 10 | 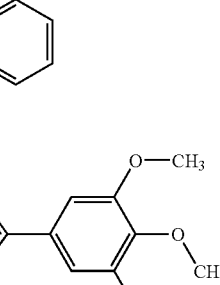 | 1.4 | 153-154° C. (dihydrochloride dihydrate) |
| 11 | 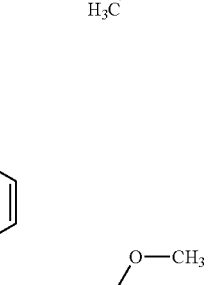 | 1.6 | 291.0-292.5° C. (hydrochloride dihydrate) |
| 12 | 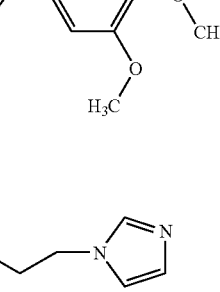 | | 161-162° C. (dihydrochloride) |

TABLE 1-continued

| | | IC50 (μM), IGF1R | Melting point |
|---|---|---|---|
| 14 | (structure) | 10 | 117-119° C. (hydrochloride) |
| 15 | (structure) | | 257-258° C. (dihydrochloride hydrate) |
| 16 | (structure) | 11 | 196-197° C. (hydrochloride) |
| 17 | (structure) | | 218-219° C. (hydrochloride) |

TABLE 1-continued

| | | IC50 (μM), IGF1R | Melting point |
|---|---|---|---|
| 18 | 4-amino-2-(4-methoxyphenyl)-1H-pyrrolo[2,3-b]pyridine | | |
| 19 | 4-amino-2-(4-methoxyphenyl)-1-(5-aminopentyl)-1H-pyrrolo[2,3-b]pyridine | | |
| 20 | 4-(hex-5-ynylamino)-2-(4-methoxyphenyl)-1H-pyrrolo[2,3-b]pyridine | 9.9 | 118-120° C. (hydrochloride hydrate) |
| 21 | 4-amino-2-[3-(3-phenylpropoxy)phenyl]-1H-pyrrolo[2,3-b]pyridine | | Oil |

TABLE 1-continued
| | IC50 (μM), IGF1R | Melting point |
|---|---|---|
| 22 | 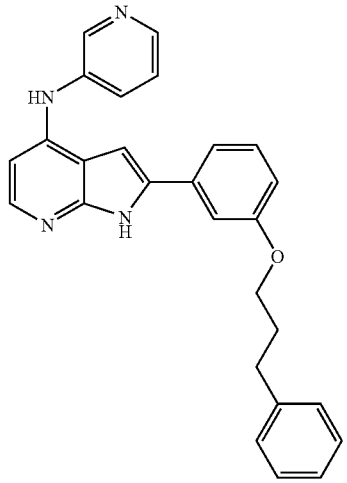 | 166-167.5° C. (2HCl) |
| 23 | 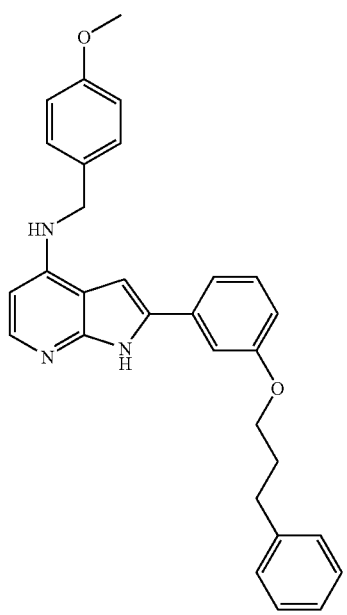 | 164-165° C. |

TABLE 1-continued
| | | IC50 (μM), IGF1R | Melting point |
|---|---|---|---|
| 24 | 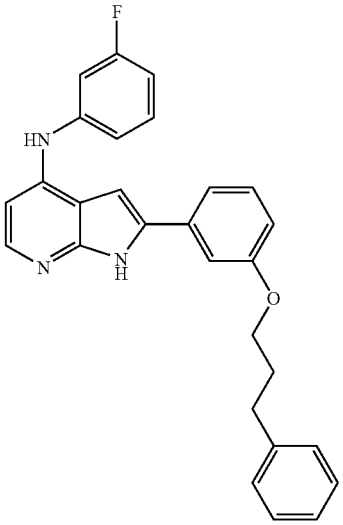 | | 210-211.5° C. (HCl) |
| 25 | 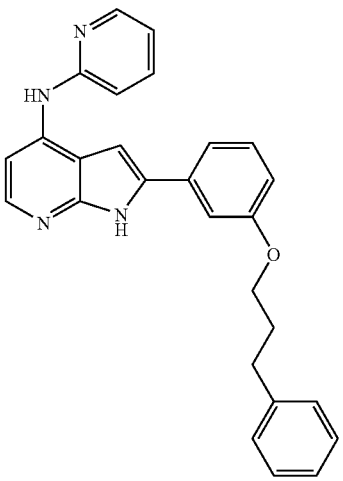 | | 175-176° C. (HCl) |
| 26 | 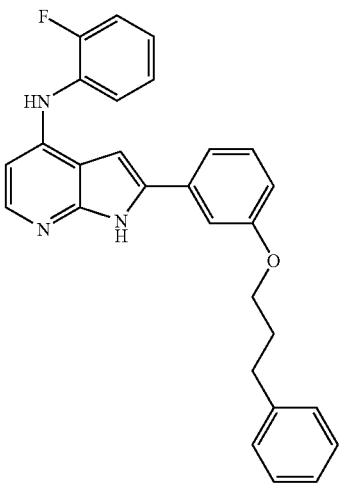 | | 155-156° C. (HCl) |

TABLE 1-continued

| | | IC50 (μM), IGF1R | Melting point |
|---|---|---|---|
| 27 | *2-(3-(3-phenylpropoxy)phenyl)-1H-pyrrolo[2,3-b]pyridine 7-oxide* | | |
| 28 | *4-chloro-2-(3-(3-phenylpropoxy)phenyl)-1H-pyrrolo[2,3-b]pyridine* | | |
| 29 | *2-(3-(benzyloxy)phenyl)-1H-pyrrolo[2,3-b]pyridine* | | |
| 30 | *2-(3-(3-phenylpropoxy)phenyl)-1H-pyrrolo[2,3-b]pyridine* | | 128-129° C. |
| 31 | *3-(1H-pyrrolo[2,3-b]pyridin-2-yl)phenol* | | 210.5-211° C. |

TABLE 1-continued
| | IC50 (μM), IGF1R | Melting point |
|---|---|---|
| 32 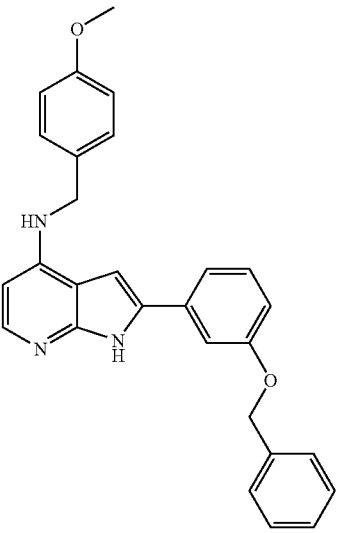 | | 218-219° C. |
| 33 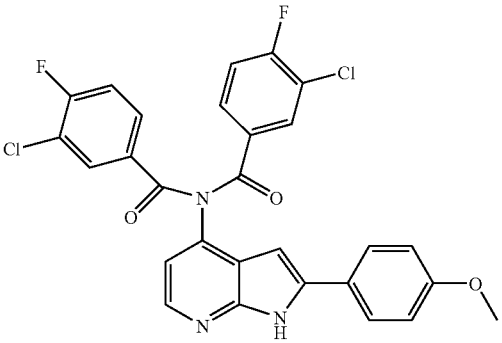 | | 142-144° C. (TFA) |
| 34 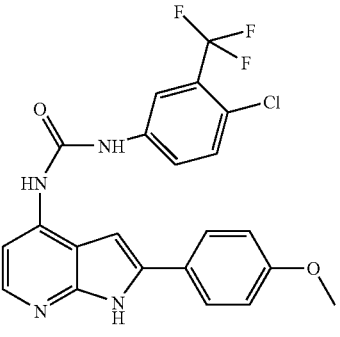 | | 141-142° C. (TFA) |
| 35 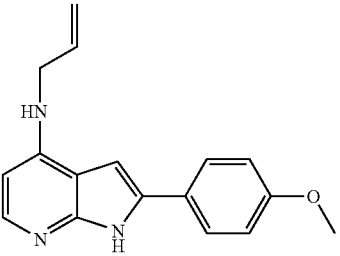 | | 189.5-190° C. (TFA) |

TABLE 1-continued

| | | IC50 (μM), IGF1R | Melting point |
|---|---|---|---|
| 36 | | | 127-127.5° C. (TFA) |
| 37 | | | 137° C. |
| 38 | | | Oil |
| 39 | | | Oil |

TABLE 1-continued

| | | IC50 (μM), IGF1R | Melting point |
|---|---|---|---|
| 40 | | | 183-184° C. (TFA) |
| 41 | | | Oil |
| 42 | | | 226-227° C. (HCl) |
| 43 | | | Oil |

TABLE 1-continued

| | | IC50 (μM), IGF1R | Melting point |
|---|---|---|---|
| 44 | | | Resin |
| 45 | | | Oil |
| 46 | | | 159.5-160° C. |
| 47 | | | 50° C. (TFA) |

TABLE 1-continued

| | | IC50 (μM), IGF1R | Melting point |
|---|---|---|---|
| 48 | (structure) | | 130-131° C. (TFA) |
| 49 | (structure) | | 129-130° C. (TFA) |
| 50 | (structure) | | 122-124° C. |

TABLE 1-continued

| | | IC50 (μM), IGF1R | Melting point |
|---|---|---|---|
| 51 | | | 130° C. (TFA, decomposition) |
| 52 | | | Oil |
| 53 | | | >299° C. |
| 54 | | | Oil |

TABLE 1-continued

| | | IC50 (μM), IGF1R | Melting point |
|---|---|---|---|
| 55 | | | 188-189° C. (TFA) |
| 56 | | | 156-158° C. |
| 57 | | | Resin |
| 58 | | | Oil |

TABLE 1-continued
| | | IC50 (µM), IGF1R | Melting point |
|---|---|---|---|
| 59 | 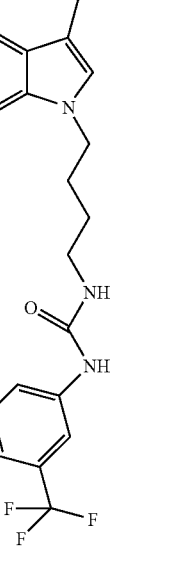 | | Oil |
| 60 | 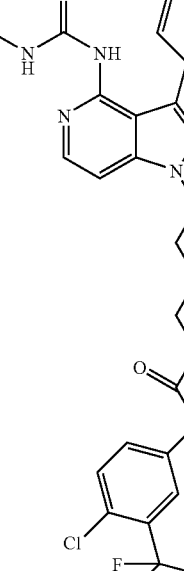 | | Oil |
| 61 | 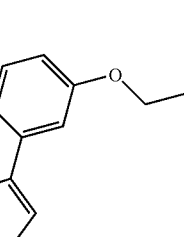 | | Resin |

TABLE 1-continued

| | | IC50 (μM), IGF1R | Melting point |
|---|---|---|---|
| 62 | | | 80° C. (decomposition) |
| 63 | | | 177-178° C. |
| 64 | | | Resin (TFA) |
| 65 | | | Resin (TFA) |

TABLE 1-continued

| | | IC50 (μM), IGF1R | Melting point |
|---|---|---|---|
| 66 | | | Resin (TFA) |
| 67 | | | Oil (TFA) |
| 68 | | 20 | Oil |
| 69 | | 5.7 | 75-78° C. |

TABLE 1-continued

| | | IC50 (μM), IGF1R | Melting point |
|---|---|---|---|
| 70 | | | 168-170° C. |
| 71 | | 4.8 | Oil |
| 72 | | 25 | |
| 73 | | 0.91 | |

TABLE 1-continued

| | | IC50 (μM), IGF1R | Melting point |
|---|---|---|---|
| 74 | | | |
| 75 | | | 205-207° C. |
| 76 | | | 179-179.5° C. |
| 77 | | | 211-212° C. |
| 78 | | | 160° C. (decomposition) |

TABLE 1-continued

| | | IC50 (μM), IGF1R | Melting point |
|---|---|---|---|
| 79 | | | 100-101° C. |
| 80 | | | 177-180° C. |
| 81 | | | Oil |
| 82 | | | 97-99° C. |

TABLE 1-continued

| | | IC50 (μM), IGF1R | Melting point |
|---|---|---|---|
| 83 | (structure) | | 225-228.5° C. |
| 84 | (structure) | | Resin |
| 85 | (structure) | | Resin |
| 86 | (structure) | | Oil |

TABLE 1-continued

| | IC50 (μM), IGF1R | Melting point |
|---|---|---|
| 87 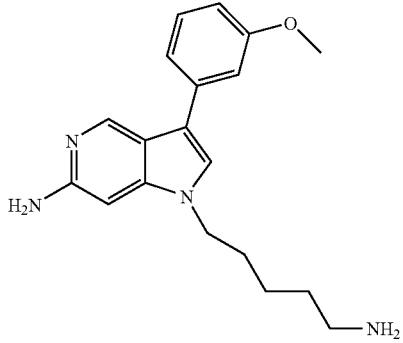 | | Oil |
| 88 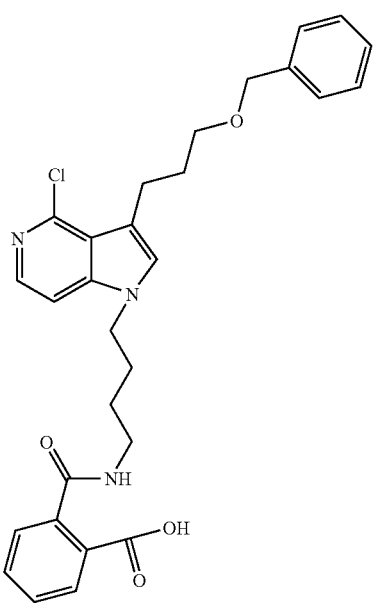 | | Oil |

Pharmaceutically or physiologically acceptable derivatives are taken to mean, for example, salts of the compounds according to the invention and also so-called prodrug compounds. Such derivatives are known in the person skilled in the art. A review of physiologically tolerated derivatives is given in Burger's Medicinal Chemistry And Drug Discovery, 5th Edition, Vol 1: Principles and Practice. Prodrug compounds are taken to mean compounds of the formula I which have been modified with, for example, alkyl or acyl groups, sugars or oligopeptides and which are rapidly cleaved or liberated in the organism to give the effective compounds according to the invention. These also include biodegradable polymer derivatives of the compounds according to the invention, as described, for example, in Int. J. Pharm. 115:61-67 (1995).

Suitable acid-addition salts are inorganic or organic salts of all physiologically or pharmacologically acceptable acids, for example halides, in particular hydrochlorides or hydrobromides, lactates, sulfates, citrates, tartrates, maleates, fumarates, oxalates, acetates, phosphates, methyl-sulfonates or p-toluenesulfonates.

Solvate of the compounds of the formula I are taken to mean adductions of inert solvent molecules onto the compounds of the formula I which form owing to their mutual attractive force. Solvate are, for example, hydrates, such as monohydrates or dihydrates, or alcoholates, i.e. addition compounds with alcohols, such as, for example, with methanol or ethanol.

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence: improved treatment, healing, prevention or elimination of a disease, syndrome, condition, complaint, disorder or prevention of side effects or also reduction in the progress of a disease, condition or disorder. The term "therapeutically effective amount" also encompasses the amounts which are effective for increasing normal physiological function.

The invention also relates to mixtures of the compounds of the formula I according to the invention, for example mixtures of two diastereomers, for example in the ratio 1:1, 12, 1:3, 1:4, 1:5, 1:10, 1:100 or 1:1000. These are particularly preferably mixtures of stereoisomeric compounds.

The present invention furthermore relates to a process for the preparation of compounds of the formula I and physiologically acceptable salts, derivatives, solvates and stereoisomers thereof, characterised in that, in a first step, a compound of the formula XI

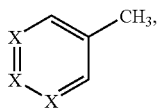

in which X has the meaning indicated above, is reacted with a compound of the formula VIII

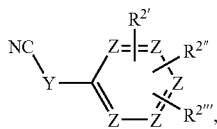

in which Z, Y and $R^2$ have the meanings indicated above, to give a compound of the formula VII

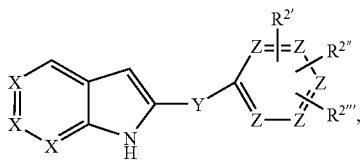

which is, if desired, reduced to give a corresponding 2,3-dihydroindole compound, and from which, in the next step, a compound of the formula VI

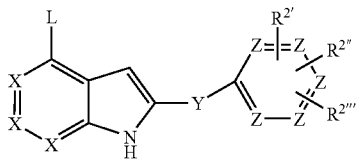

in which L is a leaving group, such as, for example, Cl, Br, I, mesylate, tosylate, phenylsulfonate or trifluoroacetate, is then prepared, and the compound of the formula VI is then, in a further step, reacted with a compound of the formula V

to give a compound of the formula IV

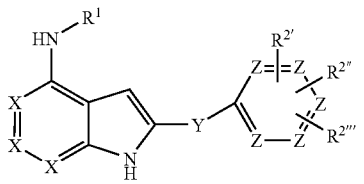

which is finally linked to a radical $R^3$ to give a compound of the formula I, and, if desired, a base or acid of the formula I is converted into one of its salts.

In a further process according to the invention for the preparation of compounds of the formula I and physiologically acceptable salts, derivatives, solvates and stereoisomers thereof, a compound of the formula (ix)

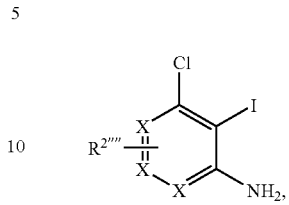

in which X has the meaning indicated for the formula I, is, in a first step, reacted with an arylsilylacetylene of the formula (viii)

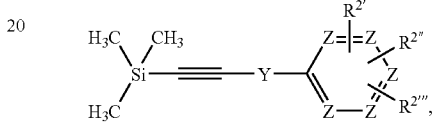

in which Z, Y and $R^2$ have the meanings indicated for the formula I, to give a compound of the formula (vii)

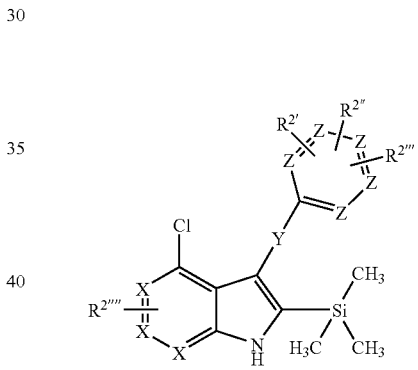

which is, if desired, reduced to give a corresponding 2,3-dihydroindole compound, which is then, in a next step, converted into a compound of the formula (vi)

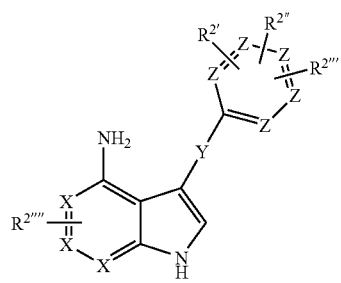

to which, if desired, a radical R¹ and/or a radical R³ is also attached to give a compound of the formula (iii)

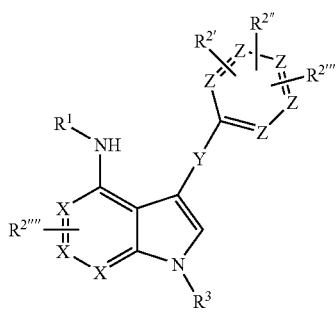

and, if desired, a base or acid of the formula (iii) is converted into one of its salts.

If it is intended to obtain compounds of the formula (ii) in which the bicyclic aryl moiety are linked to the monocyclic aryl moiety via the 2-position

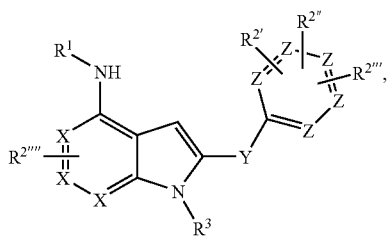

an arylacetylene containing no silyl group is employed in the first step.

The starting materials for the two process variants are generally known. If they are novel, they can be prepared by methods known per se, as described in the literature (for example in standard works, such as Houben-Weyl, Methoden der organischen Chemie [Methods of Organic Chemistry], Georg Thieme Verlag, Stuttgart; Organic Reactions, John Wiley & Sons, Inc., New York).

The compounds of the formula I and also the starting materials for their preparation are prepared by methods known per se, as described in the literature (for example in standard works, such as Houben-Weyl, Methoden der organischen Chemie [Methods of Organic Chemistry], Georg Thieme Verlag, Stuttgart; Organic Reactions, John Wiley & Sons, Inc., New York), to be precise under reaction conditions as are known and suitable for the said reactions. Use can also be made here of variants known per se which are not mentioned here in greater detail.

The azaheterocyclic compounds of the formula I can preferably be obtained by proceeding as follows:

a) A compound of the formula IX is, analogously to Davis et al. (Tetrahedron 1992, 48 (5), 939-952), initially introduced at low temperature in an inert solvent. A compound of the formula VIII is subsequently added, and the reaction mixture is stirred. When the reaction is complete, the reaction mixture is purified, and the product is isolated as a solid, preferably in crystalline form. This step may optionally be followed by reduction of the azaindole derivative formed by methods known per se (for example by selective hydrogenation) to give a 2,3-dihydroindole derivative.

b) The reaction product from step (a) is provided with a leaving group (for example Cl) in the 4-position of the indole moiety analogously to Chou et al. (J. Phys. Chem. A 2003, 107, 1459-1471).

c) The reaction product from step (b) is reacted with an amine of the formula V at elevated temperature. The product of this reaction, the desired azaheterocyclic compound of the formula I, is purified and separated off from the reaction mixture.

According to the alternative process variant (see above), a compound of the formula (vii) is obtained by reaction of a compound of the formula (ix) with a compound of the formula (viii) by the method of Larock (J. Am. Chem. Soc. 113:6689, 1991) at high temperature in an inert solvent under protective gas, where the linking between bicyclic and monocyclic aryl moieties can be controlled by the presence or absence of a silyl group in the compound of the formula (viii).

The further reaction is carried out correspondingly to step (c).

The reactions described above are generally carried out in an inert solvent. Suitable inert solvents for the reactions described above are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, N-methylpyrrolidone (NMP), dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Preference is given to sulfoxides, such as dimethyl sulfoxide (DMSO).

The amount of solvent is not crucial, 5 g to 500 g of solvent can preferably be added per g of the product to be formed.

In general, the process is carried out at a pressure of 1 to 200 bar, but preferably at atmospheric pressure.

Depending on the conditions used, the reaction temperature for the reactions described above is between about −10 and 200° C., normally between −5 and 100° C., preferably between 0 and 80° C.

Depending on the conditions used, the reaction time is between a few minutes and a number of days, preferably in the region of a number of hours.

The reaction can also be carried out in the heterogeneous phase, in which case an aqueous phase and a benzene or toluene phase are preferably used. Use is made here of a phase-transfer catalyst, such as, for example, tetrabutylammonium iodide, and optionally an acylation catalyst, such as, for example, dimethylaminopyridine.

A base of the formula I obtained can be converted into the associated acid-addition salt using an acid. Suitable for this reaction are acids which give physiologically acceptable salts. Thus, it is possible to use inorganic acids, for example sulfuric acid, hydrohalic acids, such as hydrochloric acid or hydrobromic acid, phosphoric acids, such as orthophosphoric acid, nitric acid, sulfamic acid, furthermore organic acids, in detail aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid; benzenesulfonic acid, p-toluenesulfonic acid, naphthalenemono- and -disulfonic acids, laurylsulfuric acid.

If desired, the free bases of the formula I can be liberated from their salts by treatment with strong bases, such as sodium hydroxide, potassium hydroxide, sodium carbonate or potassium carbonate, so long as no other acidic groups are present in the molecule.

Compounds of the formula I can furthermore be obtained by liberating them from one of their functional derivatives by treatment with a solvolysing or hydrogenolysing agent.

Preferred starting materials for the solvolysis or hydrogenolysis are those which otherwise conform to the formula I, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' denotes an amino-protecting group, instead of an HN group and/or those which carry a hydroxyl-protecting group instead of the H atom of a hydroxyl group, for example those which conform to the formula I, but carry a —COOR" group, in which R" denotes a hydroxyl-protecting group, instead of a —COOH group.

Preferred starting materials are also the oxadiazole derivatives, which can be converted into the corresponding amidino compounds.

It is also possible for a plurality of—identical or different—protected amino and/or hydroxyl groups to be present in the molecule of the starting material. If the protecting groups present are different from one another, they can in many cases be cleaved off selectively.

The expression "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size is furthermore not crucial; however, preference is given to those having 1-20, in particular 1-8, C atoms. The expression "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl, butyryl; aralkanoyl, such as phenylacetyl; aroyl, such as benzoyl or tolyl; aryloxy-alkanoyl, such as POA; alkoxycarbonyl, such as methoxycarbonyl, ethoxycarbonyl, 2,2,2-trichloroethoxycarbonyl, BOGC (tert-butoxycarbonyl), 2-iodoethoxycarbonyl; aralkoxycarbonyl, such as CBZ ("carbobenzoxy"), 4-methoxybenzyloxycarbonyl, FMOC; arylsulfonyl, such as Mtr. Preferred amino-protecting groups are BOC and Mtr, furthermore CBZ, Fmoc, benzyl and acetyl.

Furthermore, free amino groups can be acylated in a conventional manner using an acid chloride or anhydride or alkylated using an unsubstituted or substituted alkyl halide, or reacted with $CH_3-C(=NH)-OEt$, advantageously in an inert solvent, such as dichloromethane or THF, and/or in the presence of a base, such as triethylamine or pyridine, at temperatures between –60 and +30° C.

The expression "hydroxyl-protecting group" is likewise known in general terms and relates to groups which are suitable for protecting a hydroxyl group against chemical reactions, but which are easy to remove after the desired chemical reaction has been carried out elsewhere in the molecule. Typical of such groups are the above-mentioned unsubstituted or substituted aryl, aralkyl or acyl groups, furthermore also alkyl or silyl groups. The nature and size of the hydroxyl-protecting groups is not crucial since they are removed again after the desired chemical reaction or reaction sequence; preference is given to groups having 1-20, in particular 1-10, C atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable TFA is preferably used in excess without addition of a further solvent, perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature, RT).

The BOC, OBut and Mtr groups can, for example, preferably be cleaved off using TFA in dichloromethane or using approximately 3 to 5N HCl in dioxane at 15-30° C., the FMOC group can be cleaved off using an approximately 5 to 50% solution of dimethylamine, diethylamine or piperidine in DMF at 15-30° C.

Hydrogenolytically removable protecting groups (for example CBZ, benzyl or the liberation of the amidino group from its oxadiazole derivative) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Esters can be saponified, for example, using acetic acid or using NaOH or KOH in water, water/THF or water/dioxane, at temperatures between 0 and 100° C.

Further methods for the removal of protecting groups is described, for example, in Theodora W. Green, Peter G. M. Wuts: Protective Groups in Organic Synthesis, 3rd Edition John Wiley & Sons (1999).

Compounds of the formula I according to the invention may be chiral owing to their molecular structure and accordingly occur in various enantiomeric forms. They can therefore exist in racemic or in optically active form, Since the pharmaceutical activity of the racemates or stereoisomers of the compounds according to the invention may differ, it may be desirable to use the enantiomers. In these cases, the end product or even the intermediates can be separated into enantiomeric compounds by chemical, biochemical or physical measures known to the person skilled in the art or even employed as such in the synthesis.

After removal of the solvent, the compounds of the formula I can be obtained by conventional work-up steps, such as, for example, addition of water to the reaction mixture and extraction. It may be advantageous subsequently to carry out a distillation or crystallisation for further purification of the product.

The invention furthermore relates to medicaments comprising at least one compound according to the invention and/or physiologically acceptable salts, derivatives, solvates and stereoisomers thereof, including mixtures thereof in all ratios.

A pharmaceutical composition according to the invention may furthermore comprise further excipients and/or adjuvants and optionally one or more further medicament active ingredients.

The invention furthermore relates to a process for the preparation of a medicament, characterised in that a compound according to the invention and/or one of its physiologically acceptable salts, derivatives, solvates and stereoisomers, including mixtures thereof in all ratios, is brought into a suitable dosage form together with a solid, liquid or semi-liquid excipient or adjuvant.

The invention also relates to a set (kit) consisting of separate packs of
a) an effective amount of a compound according to the invention and/or physiologically acceptable salts, derivatives, solvates and stereoisomers thereof, including mixtures thereof in all ratios, and
b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Medicaments can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, sex, weight and condition of the patient. Preferred dosage unit formulations are those which comprise a daily dose or part-dose, as indicated above, or a corresponding fraction thereof of an active ingredient. Furthermore, medicaments of this type can be prepared using a process which is generally known in the pharmaceutical art.

Medicaments can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such medicaments can be prepared using all processes known in the pharmaceutical art by, for example, combining the active ingredient with the excipient(s) or adjuvant(s).

Medicaments adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds.

The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil, or natural sweeteners or saccharin or other artificial sweeteners, and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, poly-acetals, polydihydroxypyrans, polycyanoacrylates and crosslinked or amphipathic block copolymers of hydrogels.

Medicaments adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6):318, 1986.

Medicaments adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Medicaments adapted for topical application to the eye include eye drops, in which the active ingredient is dissolved or suspended in a suitable carrier, in particular an aqueous solvent.

Medicaments adapted for topical application in the mouth encompass lozenges, pastilles and mouthwashes.

Medicaments adapted for rectal administration can be administered in the form of suppositories or enemas.

Medicaments adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Medicaments adapted for administration by inhalation encompass finely particulate dusts or mists, which can be generated by various types of pressurised dispensers with aerosols, nebulisers or insufflators.

Medicaments adapted for vaginal administration can be administered as pessaries, tampons, creams, gels, pastes, foams or spray formulations.

Medicaments adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the medicaments according to the invention may also comprise other agents usual in the art with respect to the particular type of pharmaceutical formulation; thus, for example, medicaments which are suitable for oral administration may comprise flavours.

A therapeutically effective amount of a compound of the present invention depends on a number of factors, including, for example, the age and weight of the recipient, the precise condition that requires treatment, and its severity, the nature of the formulation and the method of administration, and is ultimately determined by the treating doctor or vet. However, an effective amount of a compound of the formula I for the treatment of the diseases according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or more usually in a series of part-doses (such as, for example, two, three, four, five or six) per day, so that the total daily dose is the same. An effective amount of a salt or solvate or of a physiologically functional derivative thereof can be determined as a fraction of the effective amount of the compound according to the invention per se.

The compounds according to the invention exhibit an advantageous biological activity which can easily be detected in enzyme assays. In such enzyme-based assays, the compounds according to the invention preferably exhibit and cause an inhibiting effect, which is usually documented by $IC_{50}$ values in a suitable range, preferably in the micromolar range and more preferably in the nanomolar range.

The present invention relates to compounds according to the invention as effectors, preferably as inhibitors of the signalling pathways described here. The invention therefore particularly preferably relates to compounds according to the invention as activators and inhibitors of tyrosine kinases, preferably as inhibitors of receptor tyrosine kinases, in particular from the insulin subfamily, which includes INS-R, IGF-IR and IR-R. The compounds according to the invention are particularly effective here in the inhibition of the receptor tyrosine kinase IGF-1R.

As discussed above, the signalling pathways influenced by the compounds according to the invention are relevant for various diseases. Accordingly, the compounds according to the invention are useful in the prophylaxis and/or treatment of diseases which are dependent on the said signalling pathways through interaction with one or more of the said signalling pathways.

The present invention therefore furthermore relates to the use of compounds according to the invention and/or physiologically acceptable salts, derivatives, solvates and stereoisomers thereof, including mixtures thereof in all ratios, for the preparation of a medicament for the treatment and/or prophylaxis of diseases, in particular diseases that are caused, mediated and/or propagated by kinases and/or by kinase-mediated signal transduction. Preference is given here to tyrosine kinases selected from the group of the receptor tyrosine kinases. Particular preference is given to IGF-1R here.

In addition, the present compounds are suitable as pharmaceutical active ingredients for mammals, in particular for humans, in the treatment of tyrosine kinase-induced diseases. The expression "tyrosine kinase-induced diseases" refers to pathological conditions which are dependent on the activity of one or more tyrosine kinases. Tyrosine kinases participate either directly or indirectly in the signal transduction pathways of a variety of cellular activities, including proliferation, adhesion and migration, as well as differentiation. Diseases associated with tyrosine kinase activity include cancer, tumour growth, arteriosclerosis, diabetic retinopathy and inflammatory diseases.

The diseases discussed here are usually divided into two groups, hyperproliferative and non-hyperproliferative diseases. In this connection, psoriasis, arthritis, inflammation, endometriosis, scarring, benign prostatic hyperplasia, immunological diseases, autoimmune diseases and immunodeficiency diseases are regarded as non-cancerous diseases, of which arthritis, inflammation, immunological diseases, autoimmune diseases and immunodeficiency diseases are usually regarded as non-hyperproliferative diseases.

In this connection, brain cancer, lung cancer, squamous cell cancer, bladder cancer, gastric cancer, pancreatic cancer, hepatic cancer, renal cancer, intestinal cancer, breast cancer, head cancer, neck cancer, oesophageal cancer, gynaecological cancer, thyroid cancer, lymphomas, chronic leukaemia and acute leukaemia are to be regarded as cancerous diseases, all of which are usually counted in the group of hyperproliferative diseases. Especially cancerous cell growth and especially cancerous cell growth mediated directly or indirectly by IGF-1R is a disease which is a target of the present invention.

The present invention therefore relates to the use of compounds according to the invention for the preparation of a medicament for the treatment and/or prophylaxis of the said diseases and also to a method for the treatment of the said diseases which comprises the administration of one or more compounds according to the invention to a patient in need of such an administration.

The recipient or patient can belong to any mammalian species, for example a primate species, particularly humans; rodents, including mice, rats and hamsters; rabbits; horses, cows, dogs, cats, etc. Animal models are of interest for experimental investigations, providing a model for the treatment of human disease.

The responsiveness of a particular cell to treatment with the compounds according to the invention can be determined by in-vitro tests. Typically, a culture of the cell is incubated with a compound according to the invention at various concentrations for a periodine of time which is sufficient to allow the active ingredients to induce cell death or to inhibit migration, usually between about one hour and one week. In-vitro tests can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the specific cell count, and may be continued until essentially no more undesired cells are detected in the body.

For the identification of kinase inhibitors, various assay systems are available. In scintillation proximity assay (Sorg et al., J. of. Biomolecular Screening: 7:11-19, 2002) and flash-plate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 191-214, 2002).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., Biochem. J. 366: 977-981, 2002).

There are many diseases and conditions associated with deregulation of cell proliferation and cell death (apoptosis). The diseases and conditions that can be treated, prevented or ameliorated by compounds according to the invention include, but are not limited to, the diseases and conditions listed below. The compounds according to the invention are suitable in the treatment and/or prophylaxis of a number of different diseases and conditions where there is proliferation and/or migration of smooth muscle cells and/or inflammatory cells into the intimal layer of a vessel, resulting in restricted blood flow through that vessel, for example in the case of neointimal occlusive lesions. Occlusive transplant vascular diseases of interest include atherosclerosis, coronary vascular disease after transplantation, vein graft stenosis, peri-anastomotic prosthetic restenosis, restenosis after angioplasty or stent placement and the like.

The present invention encompasses the use of the compounds according to the invention for the treatment or prevention of cancer. In particular, the invention relates to the use of compounds according to the invention and/or physiologically acceptable salts, derivatives, solvates and stereoisomers thereof, including mixtures thereof in all ratios, for the preparation of a medicament for the treatment and/or prophylaxis of solid tumours, where the solid tumour is particularly preferably selected from the group consisting of brain tumour, tumour of the urogenital tract, tumour of the lymphatic system, stomach tumour, laryngeal tumour, lung tumour. Solid tumours selected from the group consisting of monocytic leukaemia, lung adenocarcinoma, small-cell and non-small-cell lung carcinomas, renal cell carcinoma, endometrial carcinoma, multiple myeloma, prostate cancer, colorectal cancer, pancreatic cancer, glioblastomas and breast carcinoma can preferably also be treated with medicaments comprising compounds according to the invention.

The compounds according to the invention can be administered to patients for the treatment of cancer. By binding to IGF-1R, the present compounds inhibit tumour angiogenesis, thereby affecting the growth of tumours (S. E. Dunn et al. Mol Carcinog. January 2000; 27(1):10-7). The properties of the compounds according to the invention make the latter also appear suitable for the treatment of certain forms of blindness related to retinal neovascularisation.

The invention therefore also relates to the use of compounds according to the invention and/or physiologically acceptable salts, derivatives, solvates and stereoisomers thereof, including mixtures thereof in all ratios, for the preparation of a medicament for the treatment and or prophylaxis of diseases that are caused, mediated and/or propagated by angiogenesis.

Such a disease in which angiogenesis is implicated is an ocular disease, such as retinal vascularisation, diabetic retinopathy, age-induced macular degeneration and the like.

The invention therefore also relates to the use of the compounds according to the invention for the preparation of a medicament for the treatment and/or prophylaxis of the above diseases.

The use of compounds according to the invention and/or physiologically acceptable salts and solvates thereof for the preparation of a medicament for the treatment and/or prophylaxis of inflammatory diseases also falls within the scope of the present invention. Examples of such inflammatory diseases include rheumatoid arthritis, psoriasis, contact dermatitis, delayed hypersensitivity reaction and the like.

Preference is given to the use for the treatment of diseases, preferably from the group of hyperproliferative and non-hyperproliferative diseases. These are cancerous diseases or non-cancerous diseases.

The invention also relates to the use of compounds according to the invention and/or physiologically acceptable salts, derivatives, solvates and stereoisomers thereof, including mixtures thereof in all ratios, for the preparation of a medicament for the treatment of diseases selected from the group of non-cancerous diseases consisting of psoriasis, arthritis, inflammation, endometriosis, scarring, benign prostatic hyperplasia, immunological diseases, autoimmune diseases and immunodeficiency diseases.

The invention furthermore relates to the use of compounds according to the invention and/or physiologically acceptable salts, derivatives, solvates and stereoisomers thereof, including mixtures thereof in all ratios, for the preparation of a medicament for the treatment of diseases selected from the group of cancerous diseases consisting of brain cancer, lung cancer, squamous cell cancer, bladder cancer, gastric cancer, pancreatic cancer, hepatic cancer, renal cancer, colorectal cancer, breast cancer, head cancer, neck cancer, oesophageal cancer, gynaecological cancer, thyroid cancer, lymphoma, multiple myeloma, chronic leukaemia and acute leukaemia.

The present compounds are also suitable for combination with known anti-cancer agents. These known anti-cancer agents include the following: oestrogen receptor modulators, androgen receptor modulators, retinoid receptor modulators, cytotoxic substances, antiproliferative agents, prenyl-protein transferase inhibitors, HMG-CoA reductase inhibitors, HIV protease inhibitors, reverse transcriptase inhibitors, growth factor inhibitors and angiogenesis inhibitors. The present compounds are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl2,2-dimethyl-propanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX28-7553, trans-N-(4'-hydroxyphenyl)retinamide and N-4-carboxyphenyl-retinamide.

"Cytotoxic substances" refers to compounds which result in cell death primarily through direct action on the cellular function or which inhibit or interfere with cell mitosis, including alkylating agents, tumour necrosis factors, intercalators, microtubulin inhibitors and topoisomerase inhibitors.

Examples of cytotoxic substances include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)mu[diamine-platinum(II)]bis[diamine(chloro)platinum(II)]tetrachloride, diarisidinyispermine, arsenic trioxide, 1-(11-dodecylamino-10-hydroxyundecyl)-3,7-di-methylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPRI09881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Some examples of topoisomerase inhibitors are topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethyl-amino)ethyl]-9-hydroxy-5,6-dimethyl-6H-pyrido[4,3-b]carbazole-1-carboxamide, asulacrine, (5a,5aB,8aa, 9b)-9-[2-[N-[2-(dimethylamino)ethyl]-N-methylamino] ethyl]-5-[4-hydroxy-3,5-dimethoxyphenyl]-5,5a,6,8,8a,9-hexo-hydrofuro(3',4':6,7)naphtho(2,3-d)-1,3-dioxol-6-one, 2,3-(methylenedioxy)-5-methyl-7-hydroxy-8-methoxy-benzo[c]phenanthridinium, 6,9-bis[(2-amino-ethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]-acridin-6-one, N-[1-[2(diethylamino)ethylamino]-7-methoxy-9-oxo-9H-thio-xanthen-4-ylmethyl]formamide, N-(2-(dimethylamino)ethyl)acridine-4-carboxamide, 6-[[2-(dimethylamino)ethyl]amino]-3-hydroxy-7H-indeno-[2,1-c]quinolin-7-one and dimesna.

"Antiproliferative agents" include antisense RNA and DNA oligonucleotides such as G3139, ODN698, RVASK-RAS, GEM231 and INX3001 and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannohepto-pyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo-(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thio-semicarbazone. "Antiproliferative agents" also include monoclonal antibodies to growth factors, such as erbitux, trastuzumab, and tumour suppressor genes, such as p53, which can be delivered via recombinant virus-mediated gene transfer (see U.S. Pat. No. 6,069,134, for example).

WORKING EXAMPLES

Example A1

Preparation of 3,4,5trimethoxy-4-(1H-pyrrolo[2,3-b]pyridin-2-yl)phenol 33 ml of lithium diisopropylamide solution (1 M in THF) are initially introduced at 0° C. under nitrogen, and a solution of 3.6 g of 3-methylpyridine 1 in 50 ml of THF is added dropwise with stirring at 0-5° C. The mixture is stirred for a further 30 minutes at the temperature indicated, and a solution of 5 g of 3,4,5-trimethoxybenzonitrile in 50 ml of THF is subsequently added. The mixture is stirred at 0-5° C. for a further 1.5 h, and finally a further 33 ml of lithium diisopropylamide solution are added. The reaction mixture is subsequently warmed at 80° C. for 2 h. For work-up, the batch is allowed to cool to room temperature, and the mixture is poured onto ice. After phase separation, the mixture is extracted a further three times with 100 ml of dichloromethane each time, the combined organic phases are dried, and the solvent is removed in vacuo. The residue is purified by chromatography over a silica-gel column using ethyl acetate, giving 4.3 g of yellow crystals, which exhibit a melting point of 174.0-175.5° C.

Further compounds of the formula VII which can be prepared in this way are, for example:

2,6-dimethoxy-4-(1H-pyrrolo[2,3-b]pyridin-2-yl)phenol and 2-(1H-indol-5-yl)-1H-pyrrolo[2,3-b]pyridine Example A2

Preparation of 4-chloro-2-(3,4,5-trimethoxyphenyl)-1H-pyrrolo[2,3-b]pyridine 1.5 g of 3-chloroperbenzoic acid are added to a solution of 1 g of the 7-azaindole prepared in accordance with Example 1 in 30 ml of redistilled 1,2-dimethoxyethane, and the mixture is stirred at room temperature for a further 1.5 h. Finally, 40 ml of diethyl ether are added, and the mixture is left to stir at room temperature for a further 1.5 h. The crystals formed are filtered off with suction, washed with ether and dried in air, giving 0.9 g (56%) of yellow crystals.

A suspension of 0.9 g of the 3-chloroperbenzoate is dissolved in 10 ml of water and adjusted firstly to pH=9, then to pH=12 using a saturated potassium carbonate solution and stirred at room temperature for a further 12 h, during which crystals deposit. The crystals are filtered off with suction, washed with water and dried at 80° C. for 3 h in vacuo, giving 0.5 g (85%) of beige crystals.

500 mg of the N-oxide are heated at 110° C. for 2 h together with 10 ml of POCl₃. After the reaction mixture has cooled, it is poured into ice-water and adjusted to pH=13 using concentrated sodium hydroxide solution. The resultant precipitate is stirred with ethyl acetate, filtered off with suction through kieselguhr, and the residue is discarded. The organic phase is separated off from the filtrate, dried, and the solvent is removed in vacuo. The residue is chromatographed using ethyl acetate, and the product fractions are crystallised from ethyl acetate, giving 0.4 g (75%) of yellow crystals having a melting point of 188.0-190.0° C.

A further compound of the formula VI which can be prepared in this way is, for example, 4-chloro-2-(3-methoxyphenyl)-1H-pyrrolo[2,3-b]pyridine Example A3

Preparation of quinolin-3-yl-[2-(3,4,5-trimethoxyphenyl)-1H-pyrrolo[2,3b]pyridin-4-yl]amine 2 g of the compound of the formula VI prepared in accordance with Example 2 are dissolved in 50 ml of dioxane, 1.1 g of potassium tert-butoxide are added, and the mixture is warmed to 80° C. 20 mg of 2-(dimethyl-amino)ferrocen-1-ylpalladium(II) chloride dinorbornylphosphine complex and finally 1.15 g of 3-aminoquinoline are then added. After 12 h, the batch is allowed to cool to room temperature, and the reaction mixture is partitioned between ethyl acetate and water. The organic phase is dried, freed from solvent in vacuo and chromatographed on silica gel, giving 1.1 g of yellow crystals (melting point 279.5-280° C.). 300 mg of the product prepared in this way are dissolved in 20 ml of acetone and 20 ml of methanol, and the pH of the solution is adjusted to 3 using ethanolic hydrochloric acid. The deposited crystals are filtered off with suction washed with diethyl ether and dried in air, giving 300 mg of orange crystals. Melting point: 227.0-228.5° C.

| Elemental analysis | C | H | Cl | N |
| --- | --- | --- | --- | --- |
| Sought: | 58.0 | 5.1 | 13.7 | 10.8 |
| Found: | 57.5 | 5.3 | 13.2 | 11.0 |

(calculated on the basis of dihydrochloride hydrate)

Further compounds of the formula I which can be prepared in this way are, for example:

3-[2-(3,4,5-trimethoxyphenyl)-1H-pyrrolo[2,3-b]pyridin-4-ylamino]benzonitrile (2-pyridin-2-ylethyl)-[2-(3,4,5-trimethoxyphenyl)-1H-pyrrolo[2,3-b]pyridin-4-yl]amine (2-pyridin-3-ylethyl)-[2-(3,4,5-trimethoxyphenyl)-1H-pyrrolo[2,3-b]pyridin-4-yl]amine pyridin-3-ylmethyl-[2-(3,4,5-trimethoxyphenyl)-1H-pyrrolo[2,3-b]pyridin-4-yl]amine pyrimidin-2-yl-[2-(3,4,5-trimethoxyphenyl)-1H-pyrrolo[2,3-b]pyridin-4-yl]-amine (3-chloro-4-fluorophenyl)-[2-(3,4,5-trimethoxyphenyl)-1H-pyrrolo[2,3-b]-pyridin-4-yl]amine (3-fluorophenyl)-[2-(3,4,5-trimethoxyphenyl)-1H-pyrrolo[2,3-b]pyridin-4-yl]-amine

[4-methoxy-3-(4-methylpiperazin-1-yl)phenyl]-[2-(3,4,5-trimethoxy-phenyl)-1H-pyrrolo[2,3-b]pyridin-4-yl]amine pyridin-3-yl-[2-(3,4,5-trimethoxyphenyl)-1H-pyrrolo[2,3-b]pyridin-4-yl]-amine Example B1

Preparation of 2-chloro-3-iodopyridin-4-ylamine

Commercially available 2-chloro-4-aminopyridine (15 g, 0.1 mol) and 37.2 g (0.4 mol) of sodium carbonate are suspended in 200 ml of water and warmed to 100° C. 58.3 g (0.4 mol) of potassium iodide and 59.4 g (0.2 mol) of iodine are added to the resultant solution, and the mixture is stirred at the temperature indicated for 12 h. The mixture is subsequently adjusted to pH 13 using sodium hydroxide solution, treated with sodium thiosulfate until completely decolorised and extracted with ethyl acetate. Chromatographic purification gives 5 g (17%) of solid.

Example 82

Preparation of 4-chloro-3-(3-methoxyphenyl)-2-trimethylsilanyl-1H-pyrrolo[3,2-c]pyridine 7.6 g (30 mmol) of 2-chloro-3-iodopyridin-4-ylamine from Example B1, 1.7 g (41 mmol) of lithium chloride and 15.9 g (120 mmol) of sodium carbonate are dissolved in 100 ml of DMF, and 8 g (39 mmol) of commercial (3-methoxyphenyl)ethynyltrimethylsilane and 4.9 g (6 mmol) of commercial Pd(dppf)2Cl$_2$*H$_2$Cl$_2$ are added at 100° C. under nitrogen. The mixture is stirred at the temperature indicated for 12 h and subsequently poured at room temperature (RT) into water and extracted with ethyl acetate. The organic phase is concentrated and purified by chromatography over silica gel. The combined product fractions (5.3 g; 53%; pale-brown oil) are used for the subsequent reaction.

Example B3

Preparation of (4-methoxybenzyl)-[3-(3-methoxyphenyl)-1H-pyrrolo[3,2-c]pyridin-4-yl]amine 3 g (9 mmol) of 4-chloro-3-(3-methoxyphenyl)-2-trimethylsilanyl-1H-pyrrolo-[3,2-c]pyridine from Example B2, 1.8 g (13.5 mmol) of 4-methoxybenzyl-amine and 2.2 g (20 mmol) of potassium tert-butoxide are suspended in 50 ml of 1,4-dioxane, and 15 mg (0.02 mmol) of 2-(dimethylamino)-ferrocen-1-ylpalladium(II) chloride dinorbornylphosphine complex are added at 100° C. After 12 h, the batch is adjusted to pH 13 at RT using 1 N sodium hydroxide solution and extracted with ethyl acetate. The organic phase is purified on silica gel, the combined product fractions are re-crystallised using acetone and ethanolic hydrochloric acid, giving 500 mg (14%) of the corresponding hydrochloride.

Example B4

Preparation of tert-butyl {4-[4-(4-methoxybenzylamino)-3-(3-methoxyphenyl)pyrrolo[3,2-c]pyridin-1-yl]butyl}carbamate 450 mg (1.1 mmol) of (4-methoxybenzyl)-[3-(3-methoxyphenyl)-1H-pyrrolo-[3,2-c]pyridin-4-yl]amine from Example B3, 428 mg (1.7 mmol) of 4-(BOC-amino)butyl bromide and 0.9 g (2.8 mmol) of caesium carbonate in 60 ml of DMF are warmed to 60° C. over the course of 12 h. Aqueous work-up at RT and chromatographic purification gives 600 mg (82%) of a colourless oil.

Example C

Inhibition of IGF-1R (IC$_{50}$)

Cultivated human tumour cells which express the IGF1 receptor (IGF1R) (for example MCF-7 or Calu-6) are stimulated using human IGF1, the natural ligand of IGF1R. The stimulation induces autophosphorylation of tyrosine residues in the cytoplasmatic IGF1R domain, which triggers signal transduction cascades, which result in apoptosis inhibition and cell proliferation.

The amount of phosphorylated IGF1R is determined by a receptor-specific Capture-ELISA or an analogous LUMINEX assay. The IGF1R from cell lysates is bound to a 96-well ELISA plate or LUMINEX beads ("capturing") by means of a specific antibody, and the tyrosine phosphorylation is detected using a biotin-labelled anti-phosphotyrosine antibody and a streptavidin peroxidase conjugate by a chemoluminescence method or by means of a fluorescence-labelled anti-phosphotyrosine antibody, In order to determine the activity of kinase inhibitors, cells are pre-treated with increasing concentrations of these compounds for 45 min and subsequently stimulated using IGF1 for 5 min. As internal control, the biological activity of the ligand IGF1 is checked and a concentration series of an IGF1R reference inhibitor measured.

The following result is obtained in accordance with this procedure for quinolin-3-yl-[2-(3,4,5-trimethoxyphenyl)-1H-pyrrolo[2,3b]pyridin-4-yl]-amine: the substance inhibits the kinase IGF-1R to the extent of 50% if the compound is present in a concentration of 14 µM.

Further inhibition constants of compounds according to the invention are shown in Table 1.

The following examples relate to pharmaceutical compositions:

Example D1

Injection Vials

A solution of 100 g of an active ingredient according to the invention and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

Example D2

Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

Example D3

Solution

A solution is prepared from 1 g of an active ingredient according to the invention, 9.38 g of $NaH_2PO_4.2H_2O$, 28.48 g of $Na_2HPO_4.12\ H_2O$ and 0.1 g of benzalkonium chloride in 940 ml of bidistilled water. The pH is adjusted to 6.81 and the solution is made up to 1 l and sterilised by irradiation. This solution can be used in the form of eye drops.

Example D4

Ointment 500 mg of an active ingredient according to the invention are mixed with 99.5 g of Vaseline under aseptic conditions.

Example D5

Tablets

A mixture of 1 kg of active ingredient, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

Example D6

Dragees

Tablets are pressed analogously to Example 5e and subsequently coated in a conventional manner with a coating of sucrose, potato starch, talc, tragacanth and dye.

Example D7

Capsules 2 kg of active ingredient are introduced into hard gelatine capsules in a conventional manner in such a way that each capsule contains 20 mg of the active ingredient.

Example D8

Ampoules

A solution of 1 kg of an active ingredient according to the invention in 60 l of bidistilled water is sterile filtered, transferred into ampoules, lyophilised under sterile conditions and sealed under sterile conditions. Each ampoule contains 10 mg of active ingredient.

Should read -- 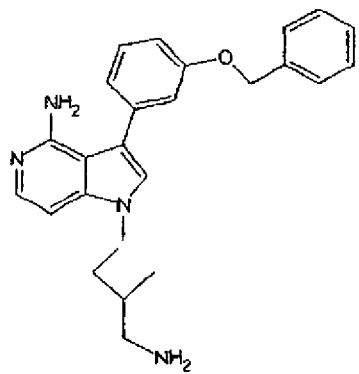

The invention claimed is:
1. A compound of formula I in which
R$^1$ denotes phenyl, phenylmethyl, pyridyl, pyridylmethyl, pyridylethyl, pyrimidyl, piperazyl, quinoliny, imidazoyl, imidazyolpropyl, pyrrolyl, pyrrolylethyl, each of which is unsubstituted or mono- or polysubstituted by Hal, cyano, methyl or methoxy, furthermore H, N,N'-dimethylaminopropyl or cyanobutyl or one of the following radicals where the linking to the remaining part of the structure of the formula I, in each case takes place via the bond to the left side as drawn, which is not a methyl group,
A denotes unbranched, branched or cyclic alkyl having 1-14 C atoms, in which one or two CH$_2$ groups may be replaced by an O or S atom and/or by an NH, NA, CONH, NHCO or —CH=CH— group and/or, in addition, 1-7 H atoms may be replaced by Hal, and in which one or two CH$_3$ groups may be replaced by NH$_2$, NAH, NA$_2$, NHCOOA, NHCONHA, NHCONHAr, or CN,
Ar denotes phenyl, which is unsubstituted or mono-, di- or trisubstituted by carbonyl oxygen, Hal, A, OH, OA, NH$_2$, NHA, NA$_2$, NO$_2$, CN, OCN, SCN, COOH, COOA, CONH$_2$, CONHA, CONA$_2$, NHCOA, NHCONH$_2$, NHSO$_2$A, CHO, COA, SO$_2$NH$_2$ and/or S(O)$_g$A, or phthalimidoyl,
Ar-A denotes aryl-alkyl
A-Ar denotes alkyl-aryl
Hal denotes F, Cl, Br or I,
X$^1$ and X$^3$ denotes CH or N, wherein one of X$^1$ and X$^3$ is N and the other of X$^1$ and X$^3$ is CH,
X$^2$ denotes CH,
Y denotes CH$_2$ or a saturated bond, Z denotes CH, R²', R²'', R²''' each, independently of one another, denote H, methoxy, ethoxy, n-propoxy, i-propoxy, 2-phenylmethoxy, 2-phenylethoxy, 3-phenylpropoxy or 4-phenylbutoxy, R²'''' denotes H, Hal, OH, CN, NH₂, unbranched or branched alkyl having 1-4, 5 or 6 C atoms, in which one CH₂ group may be replaced by an O or S atom and/or by an NH, NA, NHCO or —CH=CH— group and/or, in addition, 1-4 H atoms may be replaced by Hal, and in which one CH₃ group may be replaced by NH₂, NAH, NA₂, CN or Ar, R³ denotes H, A or Ar-A, g denotes 0, 1 or 2 and ---- denotes a single or double bond, or a pharmaceutically acceptable salt thereof.

2. A compound according to claim 1, which is of formula AII

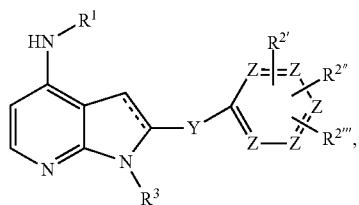

AII in which R¹, R²', R²'', R²''', R³, Y and Z have the meaning indicated for formula I.

3. A compound according to claim 1, which is of formula AIII

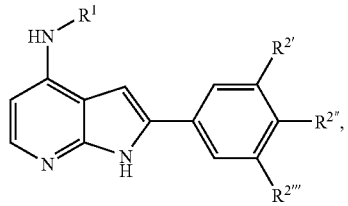

AIII in which R¹, R²', R²'', and R²''' have the meaning indicated for formula I.

4. A compound according to claim 1, which is of formula BII

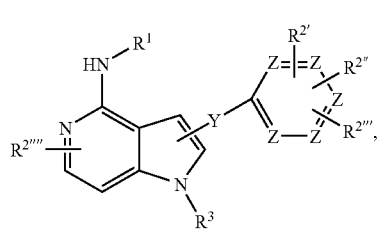

BII in which R¹, R²', R²'', R²''', R²'''', R³, Y and Z have the meaning indicated for formula I.

5. A compound according to claim 1, which is of formula BIII

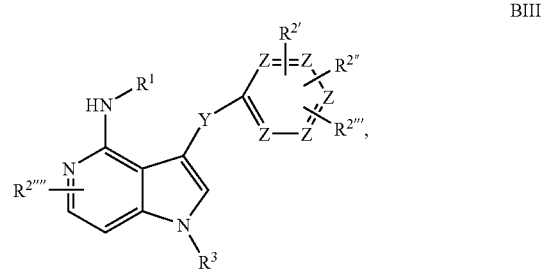

BIII in which R¹, R²', R²'', R²''', R²'''', R³, Y and Z have the meaning indicated for the formula I.

6. A compound according to claim 1, in which

I)
R¹ denotes phenyl, phenylmethyl, pyridyl, pyridylmethyl, pyridylethyl, pyrimidyl, piperazyl, quinoliny, imidazoyl, imidazyolpropyl, pyrrolyl, or pyrrolylethyl, each of which is unsubstituted or mono- or polysubstituted by Hal, cyano, methyl or methoxy, or denotes H, or
II)
R²', R²'', R²''' each, independently of one another, denote H, methoxy, ethoxy, n-propoxy, or i-propoxy, R²'''' denotes H, Hal or NH₂, or
III)
one of the radicals R²', R²'', R²''' denotes methoxy and the other two denote H, or
IV)
R³ denotes 2-aminoethyl, 3-aminopropyl, 4-aminobutyl, 5-aminopentyl, 3-aminomethylcyclobutyl, (isoindole-1,3-dion)-2-yl or 4-(tert-butyl carbamate) but-1-yl, or
V)
R²', R²'', R²''' each, independently of one another, denotes H, methoxy, ethoxy, n-propoxy, i-propoxy, 2-phenylmethoxy or 2-phenylethoxy, R²'''' denotes H, Cl or NH₂, R¹ denotes phenyl, phenylmethyl, pyridyl, pyridylmethyl, pyridylethyl, pyrimidyl, piperazyl, quinoliny, imidazoyl, imidazyolpropyl, pyrrolyl, or pyrrolylethyl, each of which is unsubstituted or mono- or polysubstituted by Hal, cyano, methyl or methoxy, or denotes H, and R³ denotes 2-aminoethyl, 3-aminopropyl, 4-aminobutyl, 5-aminopentyl, 3-aminomethylcyclobutyl, (isoindole-1,3-dion)-2-yl or 4-(tert-butyl carbamate) but-1-yl, or
VI)
one of the radicals R²', R²''', R²'''' denotes methoxy and the other two denote H R¹ denotes H, pyridyl, pyridylmethyl or (4-methoxyphenyl)methyl, and R³ denotes 2-aminoethyl, 3-aminopropyl, 4-aminobutyl, 5-aminopentyl, 3-aminomethylcyclobutyl, (isoindole-1,3-dion)-2-yl or 4-(tert-butyl carbamate) but-1-yl, or
VII)
one of the radicals R²', R²'', R²''' denotes methoxy or 2-phenylmethoxy and the other two denote H R¹ denotes H, pyrid-2 or 3-yl, pyrid-2 or 3-ylmethyl or (4-methoxyphenyl)methyl, and R³ denotes 2-aminoethyl, 3-amino-n-propyl, 4-amino-n-butyl, 5-amino-n-pentyl, 3-aminomethylcyclobut-1-yl, (isoindole-1,3-dion)-2-yl or 4-(tert-butyl carbamate)but-1-yl.

7. A process for preparing a compound of claim 1, comprising reacting a compound of formula (ix)

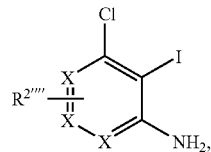

in which X has the meaning indicated for formula I, with a compound of formula (viii)

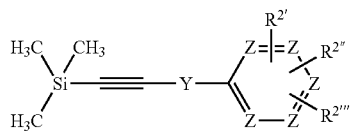

in which Z, Y and R² have the meanings indicated for formula I, to give a compound of formula (vii)

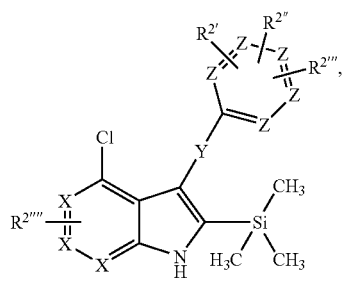

which is optionally reduced to give a corresponding 2,3-dihydroindole compound, which is, in a next step, converted into a compound of formula (vi)

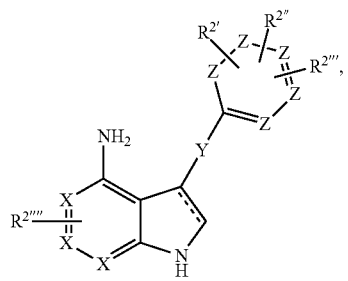

to which optionally a radical R¹ and/or a radical R³ is also attached to give a compound of formula (iii)

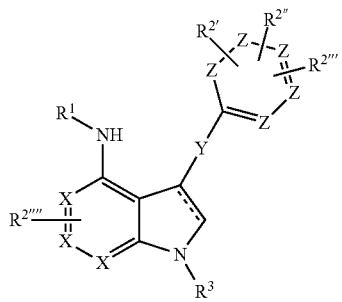

and optionally a base or acid of the formula (iii) is converted into one of its salts, or where the linking of the monocyclic aryl moiety to the bicyclic aryl moiety via its 2-position to give a compound of the formula (ii)

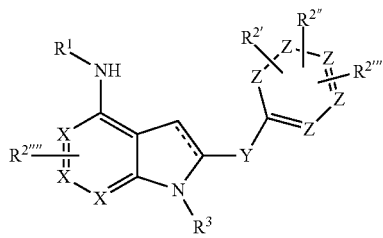

optionally, a compound of formula (viii) containing no silyl group is employed in the first reaction step above.

8. A pharmaceutical composition, comprising at least one compound according to claim 1 and one or more pharmaceutically acceptable excipients and/or adjuvants.

9. A pharmaceutically acceptable salt of a compound of claim 1.

10. A compound according to claim 1, which is (3-fluorophenyl)-[2-(3,4,5-trimethoxy-phenyl)-1H-pyrrolo[2,3-b]pyridin-4-yl]amine.

11. A compound according to claim 1, wherein

A denotes unbranched, branched or cyclic alkyl having 1-14 C atoms, in which one or two $CH_2$ groups may be replaced by an O or S atom and/or by an NH, CONH, NHCO or —CH=CH— group and/or, in addition, 1-7 H atoms may be replaced by Hal, and in which one or two $CH_3$ groups may be replaced by $NH_2$ or CN.

12. A compound according to claim 1, wherein

A denotes unbranched, branched or cyclic alkyl having 1-14 C atoms, in which one or two $CH_2$ groups may be replaced by an S atom and/or by an NH, CONH, NHCO or —CH=CH— group and/or, in addition, 1-7 H atoms may be replaced by Hal, and in which one or two $CH_3$ groups may be replaced by $NH_2$ or CN.

13. A compound according to claim 1, wherein

Y denotes a saturated bond.

14. A compound according to claim 1, wherein

R³ denotes H or Ar-A.

15. A compound, which is

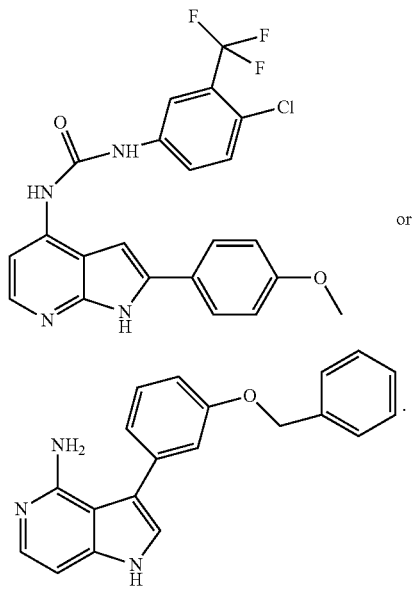

16. A compound according to claim 15, which is

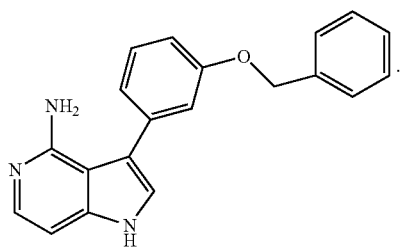

17. A compound according to claim 1, in which

Ar denotes phenyl, which is unsubstituted or mono-, di- or trisubstituted by carbonyl oxygen, Hal, A, OH, OA, NH$_2$, NHA, NA$_2$, NO$_2$, CN, OCN, SCN, COOH, COOA, CONH$_2$, CONHA, CONA$_2$, NHCOA, NHCONH$_2$, NHSO$_2$A, CHO, COA, SO$_2$NH$_2$ and/or S(O)$_g$A.

18. A compound according to claim 15, which is

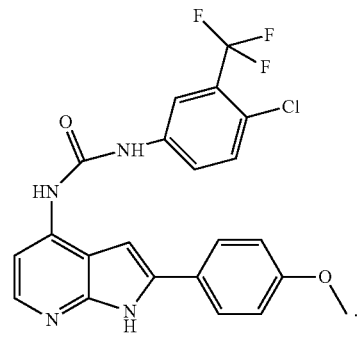

19. A compound, which is one of the following compounds

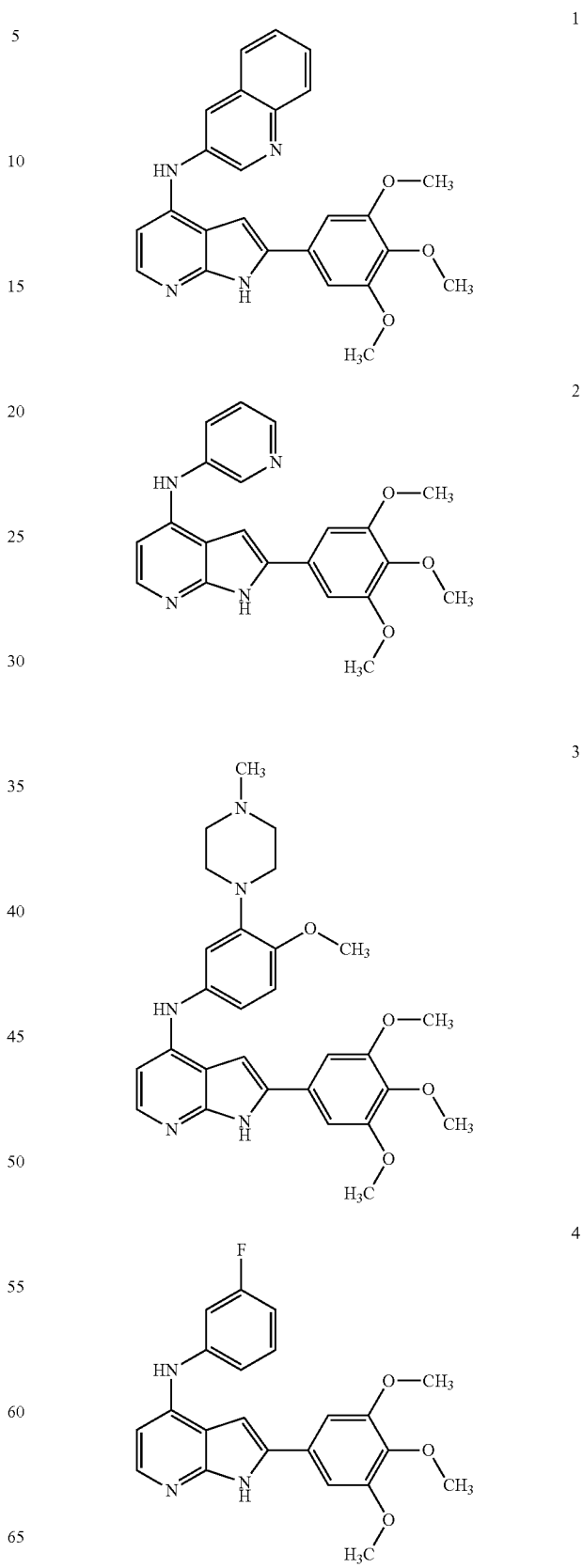

5
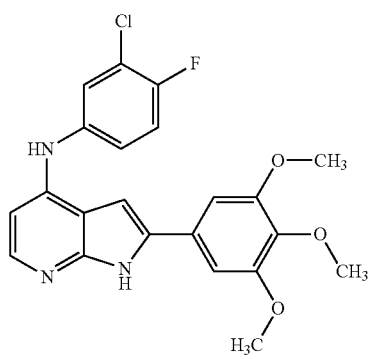 [SMILES: COc1cc(-c2cc3c(Nc4ccc(F)c(Cl)c4)ccnc3[nH]2)cc(OC)c1OC]
6
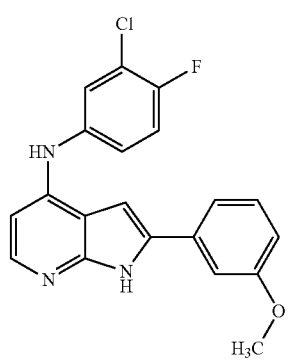 [SMILES: COc1cccc(-c2cc3c(Nc4ccc(F)c(Cl)c4)ccnc3[nH]2)c1]
7
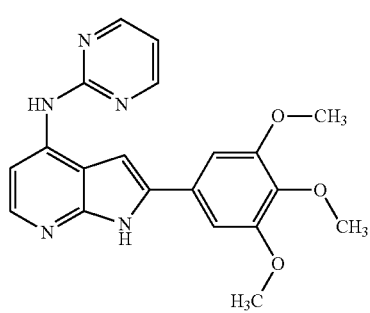 [SMILES: COc1cc(-c2cc3c(Nc4cnccn4)ccnc3[nH]2)cc(OC)c1OC]
8
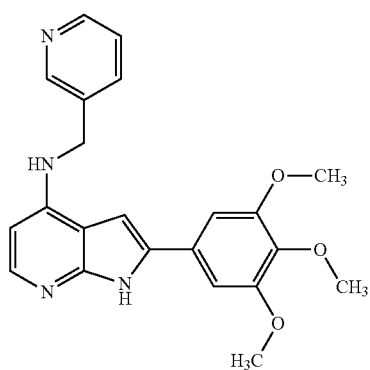 [SMILES: COc1cc(-c2cc3c(NCc4cccnc4)ccnc3[nH]2)cc(OC)c1OC]
9
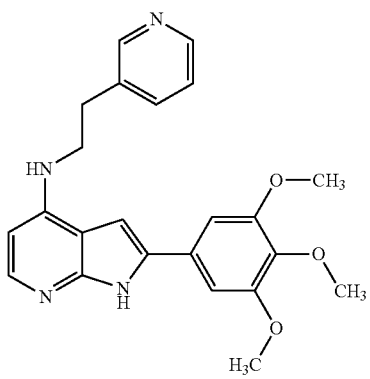 [SMILES: COc1cc(-c2cc3c(NCCc4cccnc4)ccnc3[nH]2)cc(OC)c1OC]
10
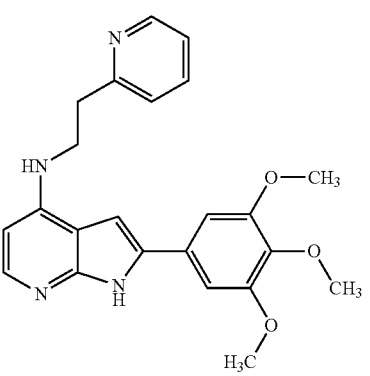 [SMILES: COc1cc(-c2cc3c(NCCc4ccccn4)ccnc3[nH]2)cc(OC)c1OC]
11
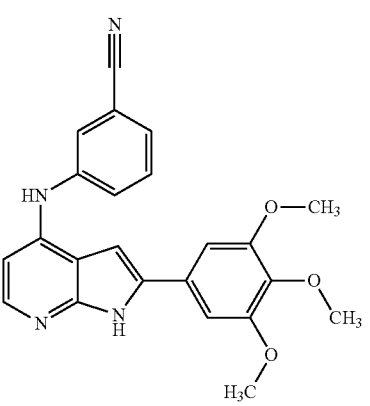 [SMILES: COc1cc(-c2cc3c(Nc4cccc(C#N)c4)ccnc3[nH]2)cc(OC)c1OC]
12
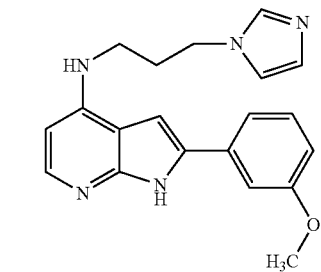

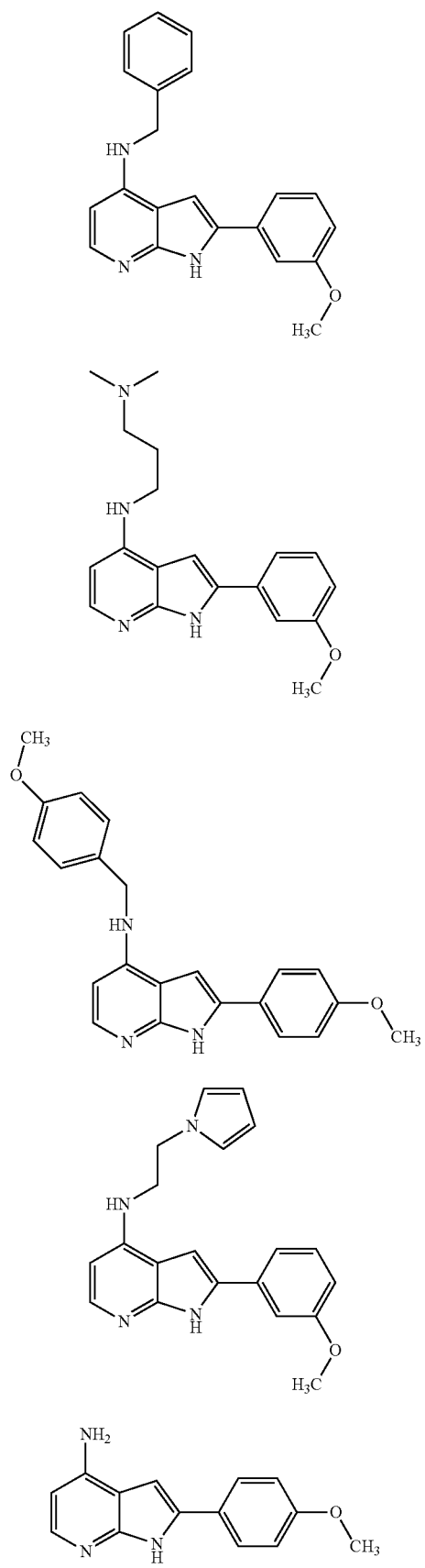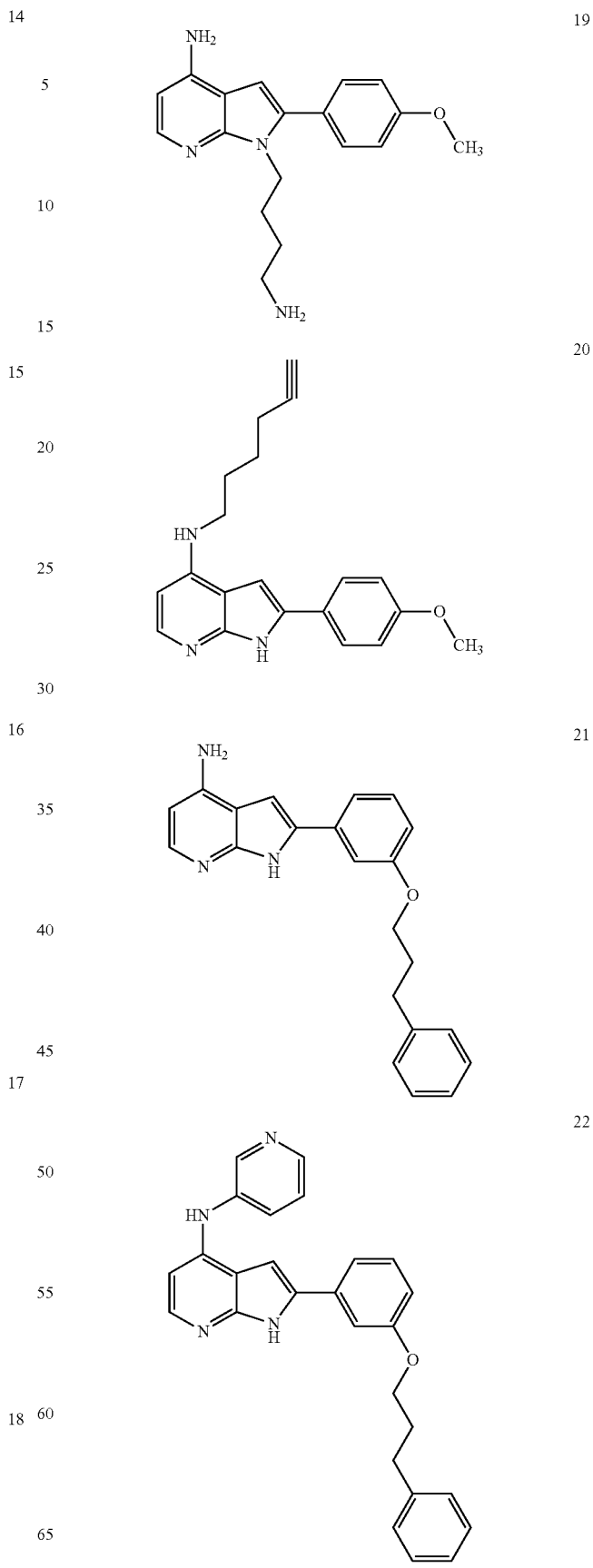

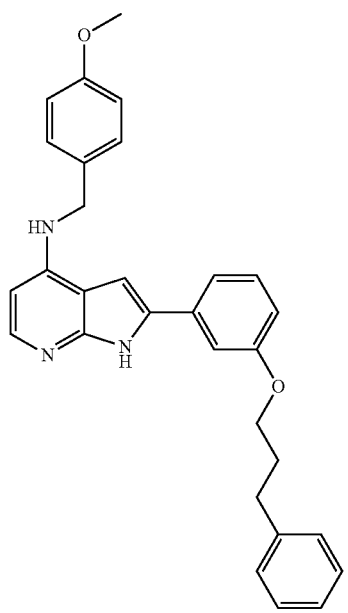 [SMILES: COc1ccc(CNc2ccnc3[nH]c(-c4cccc(OCCCc5ccccc5)c4)cc23)cc1]
23
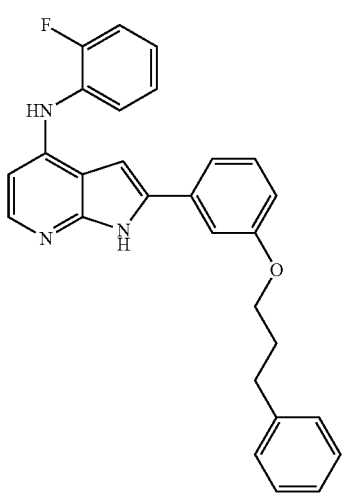
26
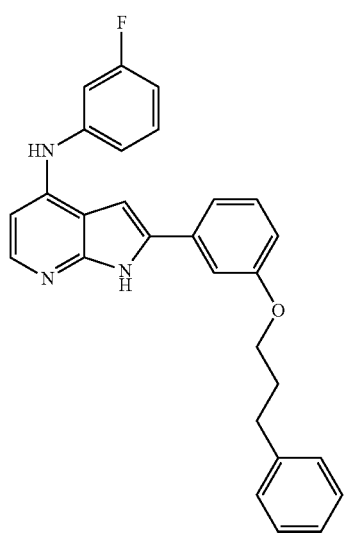 [SMILES: Fc1cccc(Nc2ccnc3[nH]c(-c4cccc(OCCCc5ccccc5)c4)cc23)c1]
24
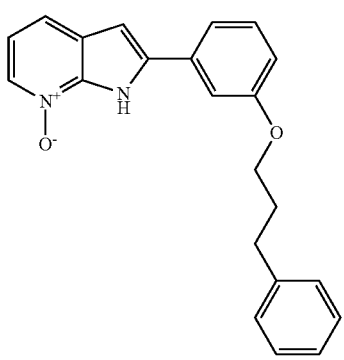 [SMILES: [O-][n+]1cccc2cc(-c3cccc(OCCCc4ccccc4)c3)[nH]c21]
27
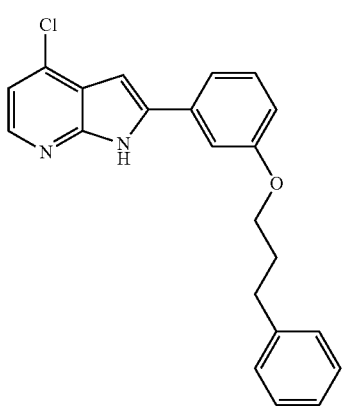 [SMILES: Clc1ccnc2[nH]c(-c3cccc(OCCCc4ccccc4)c3)cc12]
28
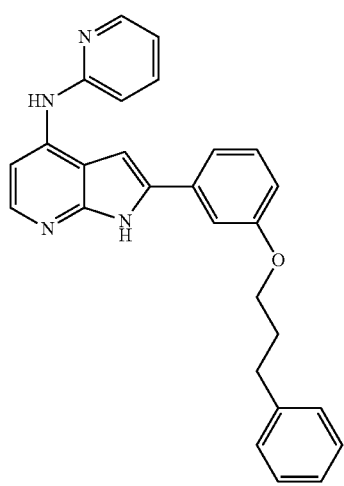
25
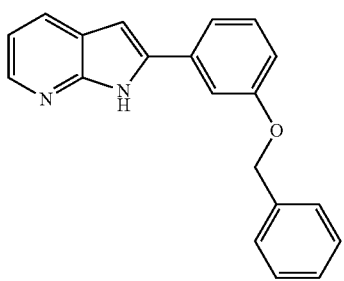 [SMILES: c1ccc(COc2cccc(-c3cc4cccnc4[nH]3)c2)cc1]
29

| 91 | 92 |
|---|---|
| 30 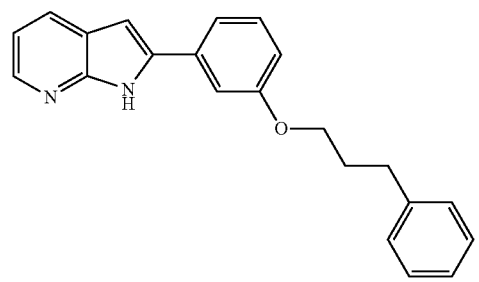 [SMILES: c1ccc(CCCOc2cccc(-c3cc4cccnc4[nH]3)c2)cc1] | 35 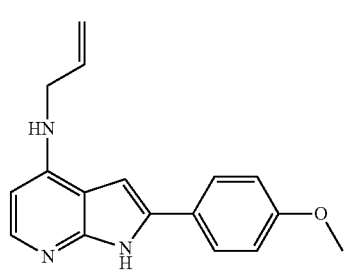 [SMILES: C=CCNc1ccnc2[nH]c(-c3ccc(OC)cc3)cc12] |
| 31 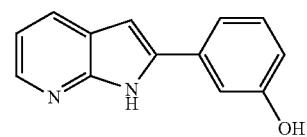 | 36 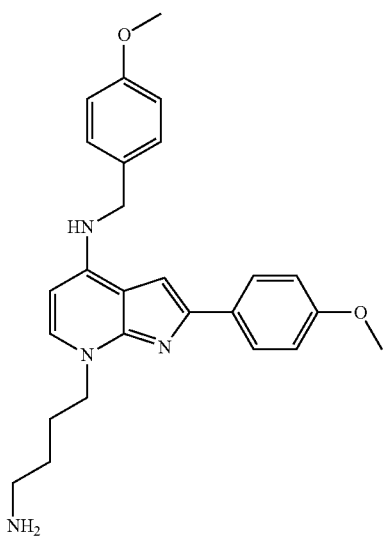 [SMILES: COc1ccc(CNc2ccn(CCCCN)c3nc(-c4ccc(OC)cc4)cc2-3)cc1] |
| 32 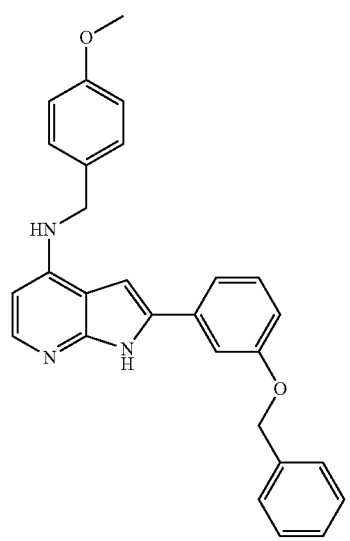 | 37 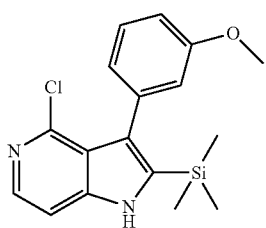 [SMILES: COc1cccc(-c2c([Si](C)(C)C)[nH]c3ccnc(Cl)c23)c1] |
| 33 | 38 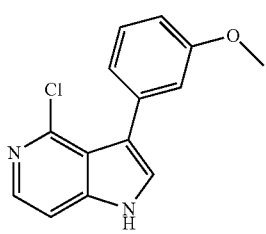 [SMILES: COc1cccc(-c2c[nH]c3ccnc(Cl)c23)c1] |
| 34 | |

39
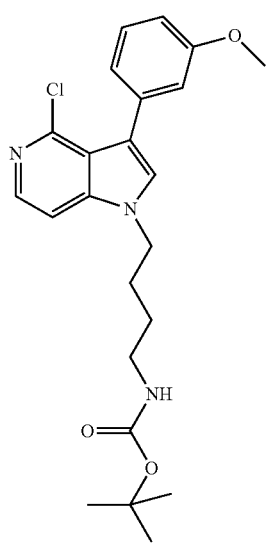 [SMILES: COc1cccc(-c2cn(CCCCNC(=O)OC(C)(C)C)c3ccnc(Cl)c23)c1]
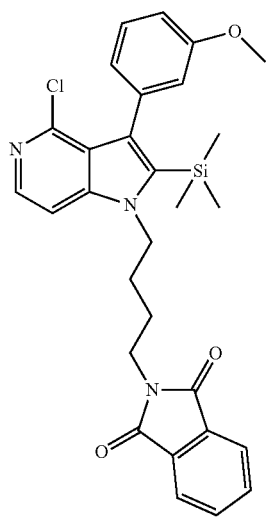
41
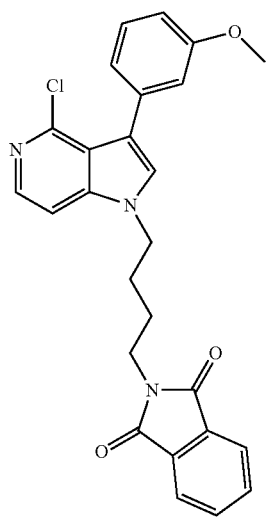
42
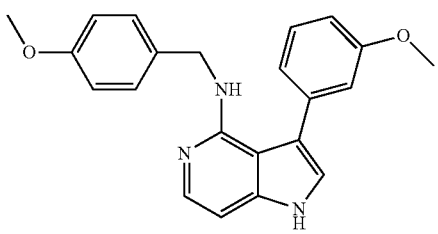
43
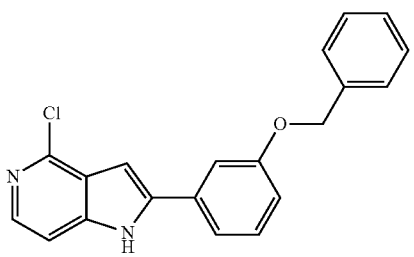 [SMILES: Clc1nccc2[nH]c(-c3cccc(OCc4ccccc4)c3)cc12]
44
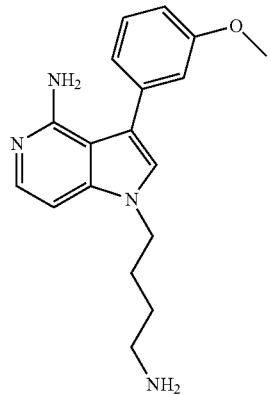 [SMILES: COc1cccc(-c2cn(CCCCN)c3ccnc(N)c23)c1]
45
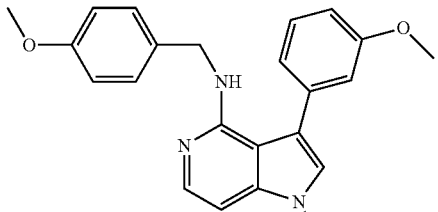
46
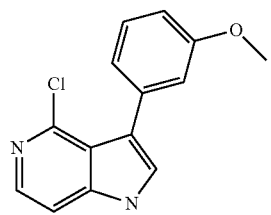

47
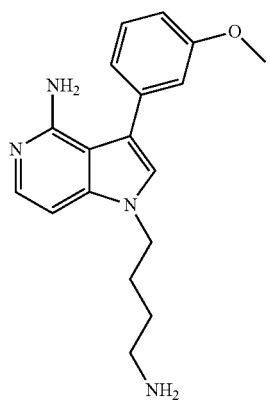 [SMILES: COc1cccc(-c2cn(CCCCN)c3ccnc(N)c23)c1]
48
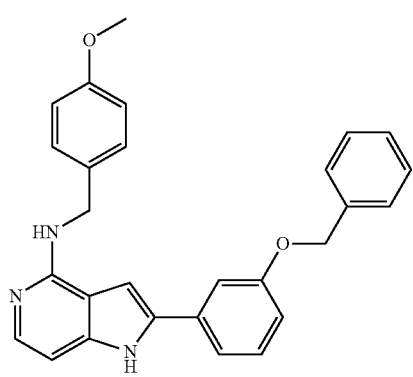 [SMILES: COc1ccc(CNc2nccc3[nH]c(-c4cccc(OCc5ccccc5)c4)cc23)cc1]
49
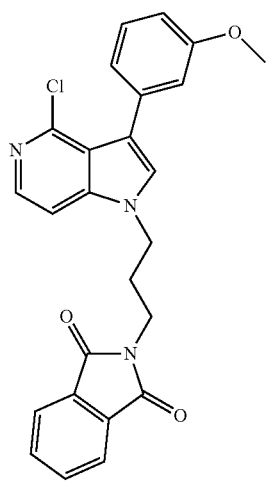
50
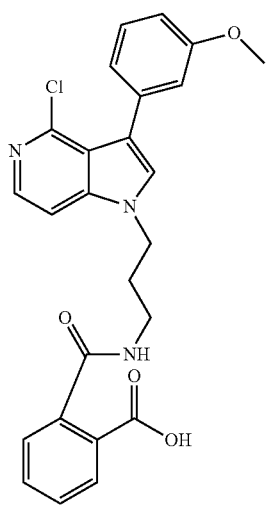
51
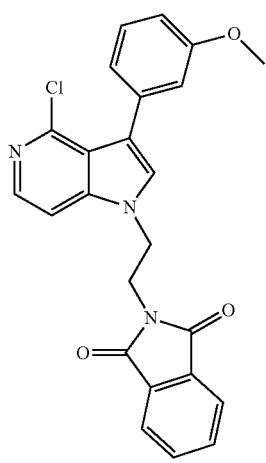 [SMILES: COc1cccc(-c2cn(CCN3C(=O)c4ccccc4C3=O)c3ccnc(Cl)c23)c1]
52
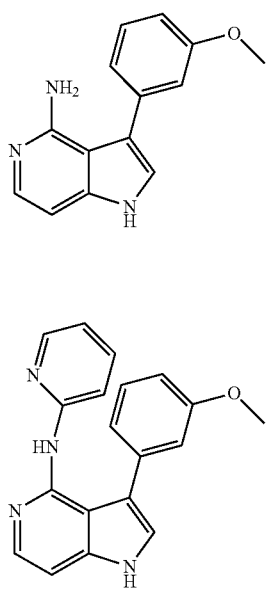
53

54
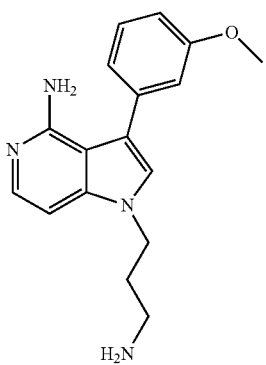 [SMILES: COc1cccc(-c2cn(CCCN)c3ccnc(N)c23)c1]
55
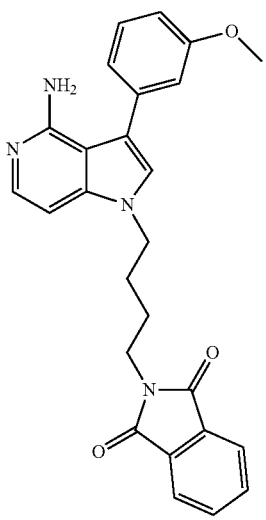
56
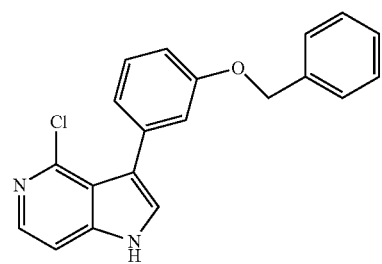
57
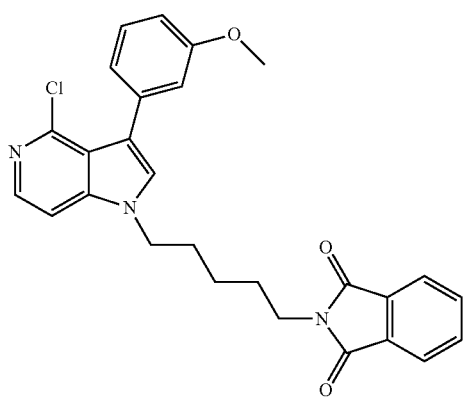
58
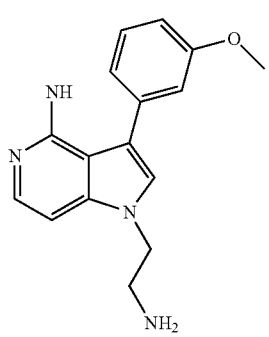 [SMILES: COc1cccc(-c2cn(CCN)c3ccnc(N)c23)c1]
59
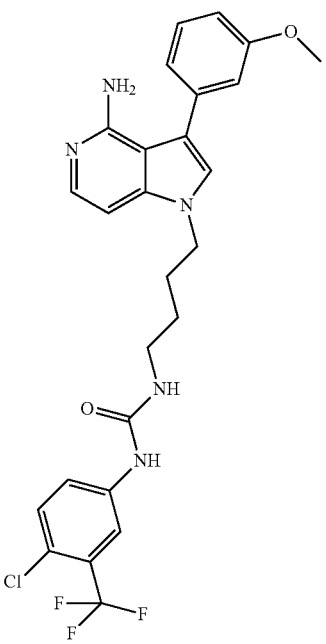
60
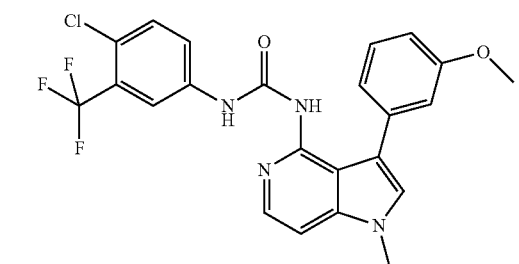
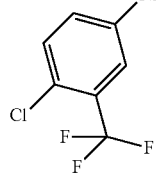

| 61 | 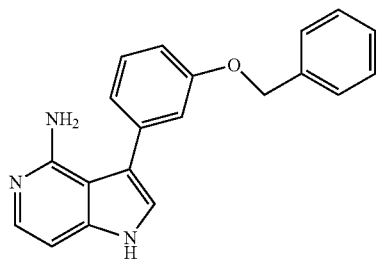 | 65 | 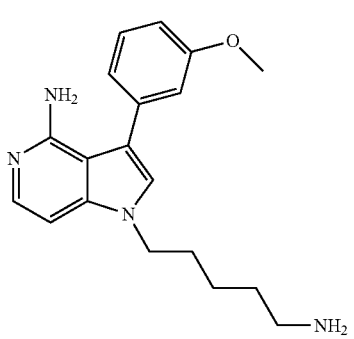 |
| 62 | 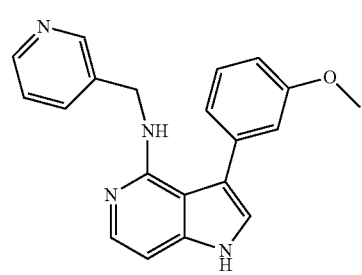 [SMILES: COc1cccc(-c2c[nH]c3ccnc(NCc4cccnc4)c23)c1] | 66 | 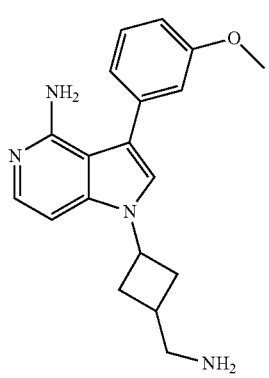 |
| 63 | 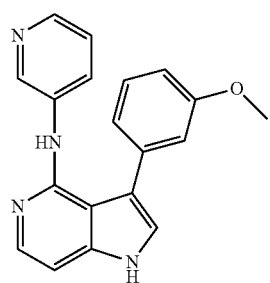 | 67 | 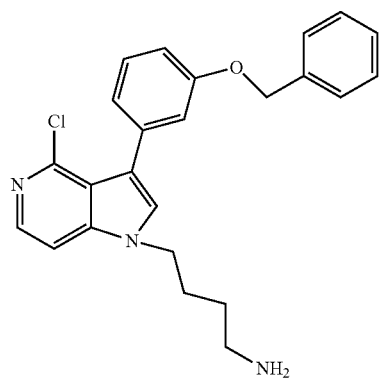 |
| 64 | 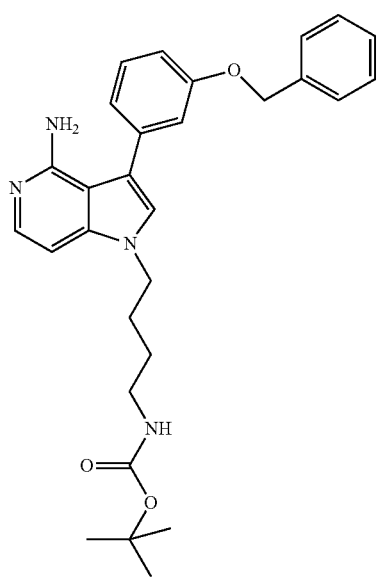 | 68 | 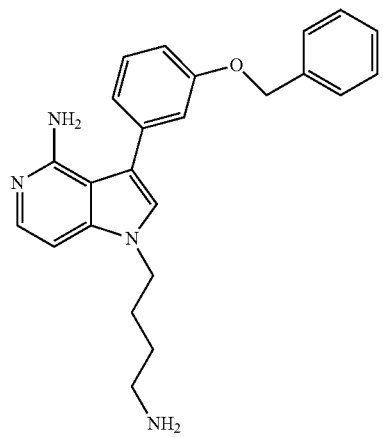 |

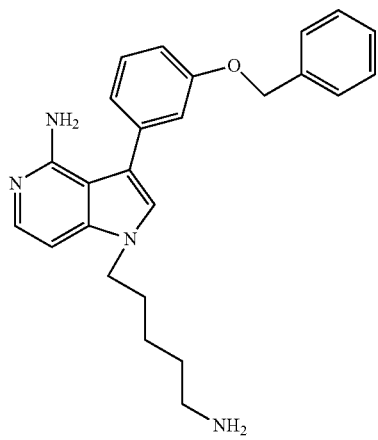
69
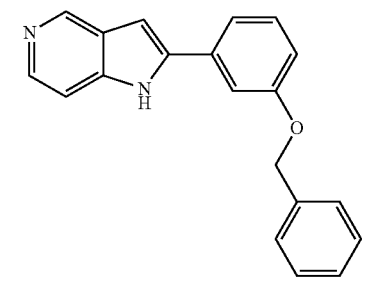 [SMILES: c1ccc(COc2cccc(-c3cc4cnccc4[nH]3)c2)cc1]
70
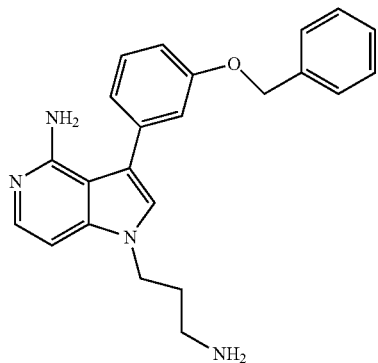
71
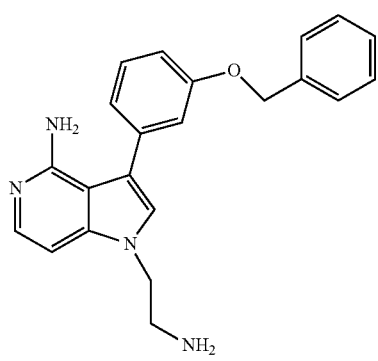
72
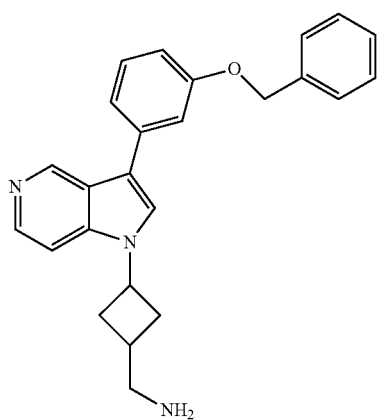
73
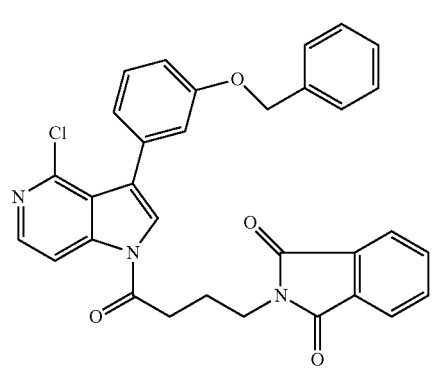
74
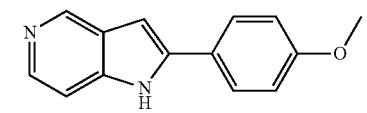
75
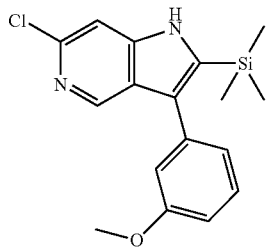
76
77

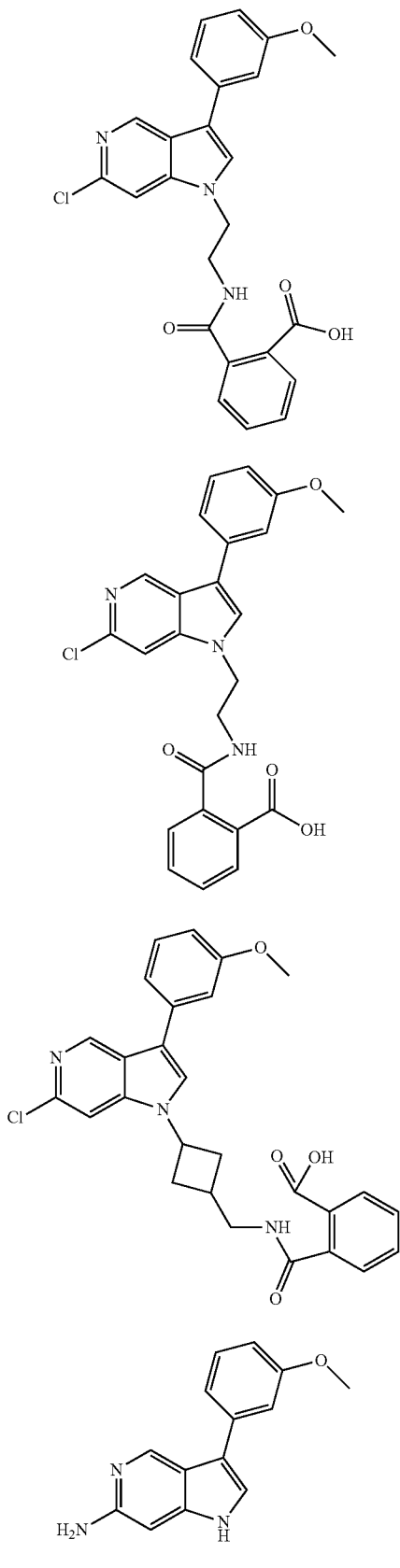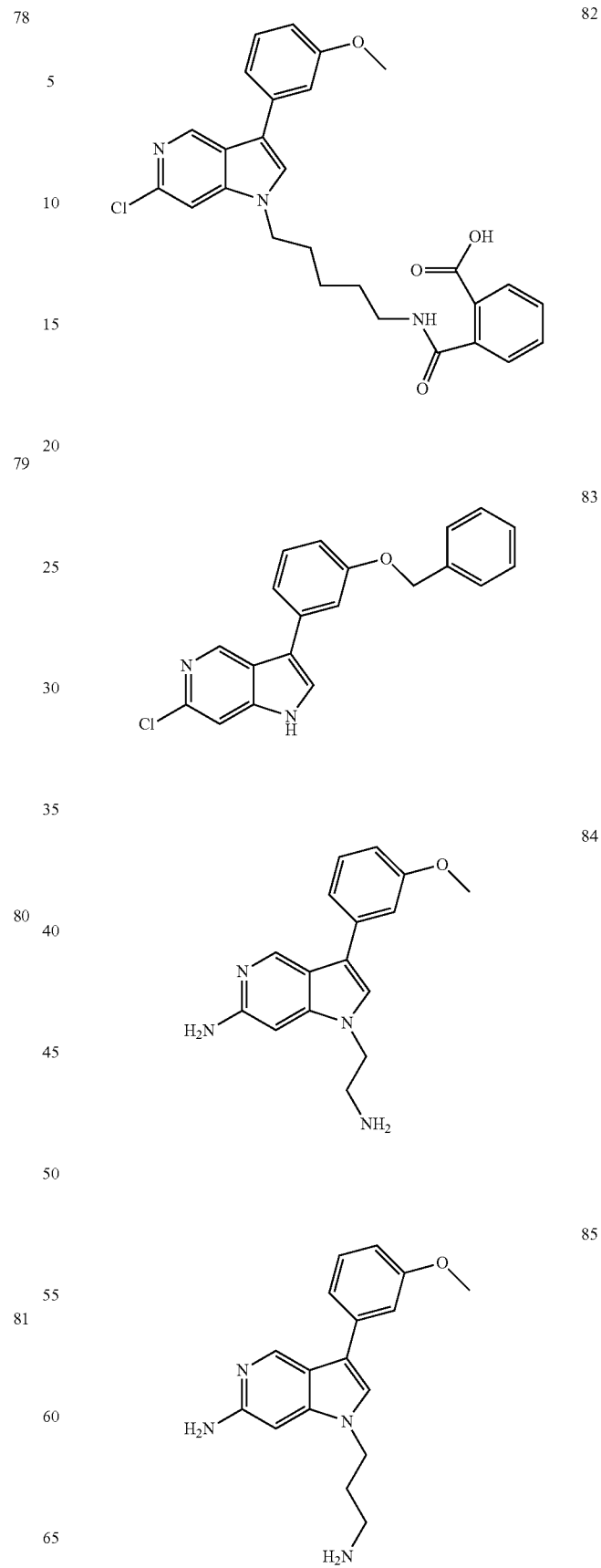

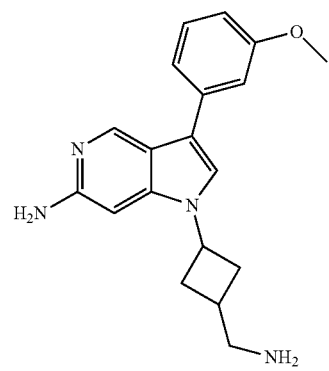
86
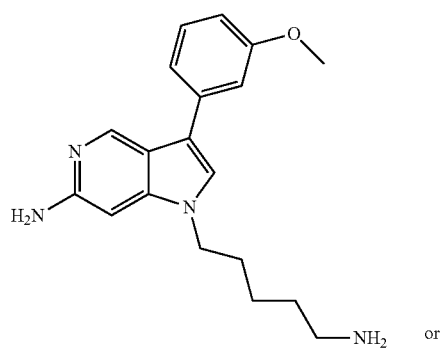
87
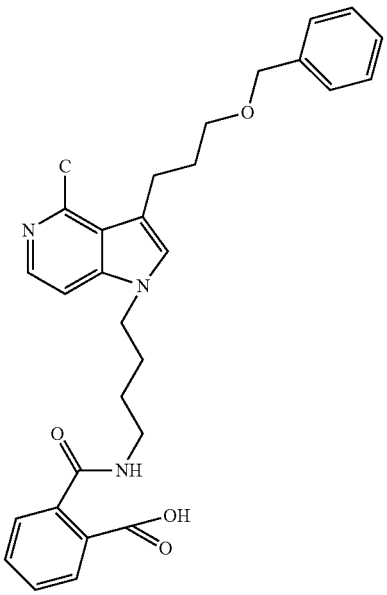
88
or a pharmaceutically acceptable salt thereof.
20. A compound according to claim 19, which is one of compounds 27-31, 37-41, 43, 44, 46, 47, 49-52, 54-59, 61 or 64-81 or a pharmaceutically acceptable salt thereof.
21. A compound according to claim 19, which is one of compounds 1-12, 24-26, 32-36, 42, 45, 48, 53, 60, 62, 63 or 82-88 or a pharmaceutically acceptable salt thereof.
* * * * *

UNITED STATES PATENT AND TRADEMARK OFFICE
CERTIFICATE OF CORRECTION

PATENT NO. : 8,859,581 B2
APPLICATION NO. : 11/912462
DATED : October 14, 2014
INVENTOR(S) : Heinrich et al.

Page 1 of 2

It is certified that error appears in the above-identified patent and that said Letters Patent is hereby corrected as shown below:

In the Claims

Column 101, structure 72 reads " 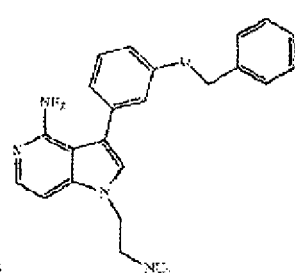 "

Should read -- 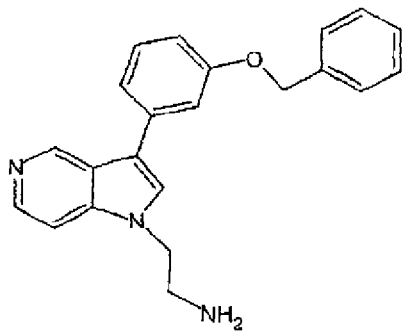

Column 102, structure 73 reads " 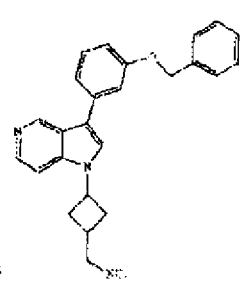 "

Signed and Sealed this
Twenty-fifth Day of August, 2015

Michelle K. Lee
*Director of the United States Patent and Trademark Office*

CERTIFICATE OF CORRECTION (continued)
U.S. Pat. No. 8,859,581 B2